(12) United States Patent
Gach et al.

(10) Patent No.: US 11,878,188 B2
(45) Date of Patent: Jan. 23, 2024

(54) SYSTEMS AND METHODS FOR REAL-TIME B0 FLUCTUATION COMPENSATION

(71) Applicant: Washington University, St. Louis, MO (US)

(72) Inventors: H. Michael Gach, St. Louis, MO (US); Austen Curcuru, St. Louis, MO (US); Taeho Kim, St. Louis, MO (US); Umberto Villa, St. Louis, MO (US)

(73) Assignee: Washington University, St. Louis, MO (US)

( * ) Notice: Subject to any disclaimer, the term of this patent is extended or adjusted under 35 U.S.C. 154(b) by 72 days.

(21) Appl. No.: 17/736,088

(22) Filed: May 3, 2022

(65) Prior Publication Data
US 2022/0347492 A1    Nov. 3, 2022

Related U.S. Application Data

(60) Provisional application No. 63/183,521, filed on May 3, 2021.

(51) Int. Cl.
*A61N 5/10* (2006.01)
*G06T 11/00* (2006.01)
*G01R 33/565* (2006.01)
*G01R 33/56* (2006.01)

(52) U.S. Cl.
CPC ......... *A61N 5/1049* (2013.01); *G01R 33/565* (2013.01); *G01R 33/5608* (2013.01); *G06T 11/005* (2013.01); *A61N 2005/1055* (2013.01)

(58) Field of Classification Search
CPC .............. G01R 33/5608; G01R 33/565; A61N 2005/1055; A61N 5/1049; G06T 11/005
See application file for complete search history.

(56) References Cited

U.S. PATENT DOCUMENTS

| 11,002,817 | B2* | 5/2021 | Guo ................... G01R 33/5676 |
| 2011/0156703 | A1* | 6/2011 | O'Connor ............ A61N 5/1049 324/307 |
| 2022/0203132 | A1* | 6/2022 | Torres .................. A61N 5/1067 |

* cited by examiner

*Primary Examiner* — Gregory H Curran

(57) ABSTRACT

Devices, systems, and methods for enhancing MRI image quality and tracking accuracy in MR-guided treatment systems are described.

6 Claims, 22 Drawing Sheets
(18 of 22 Drawing Sheet(s) Filed in Color)

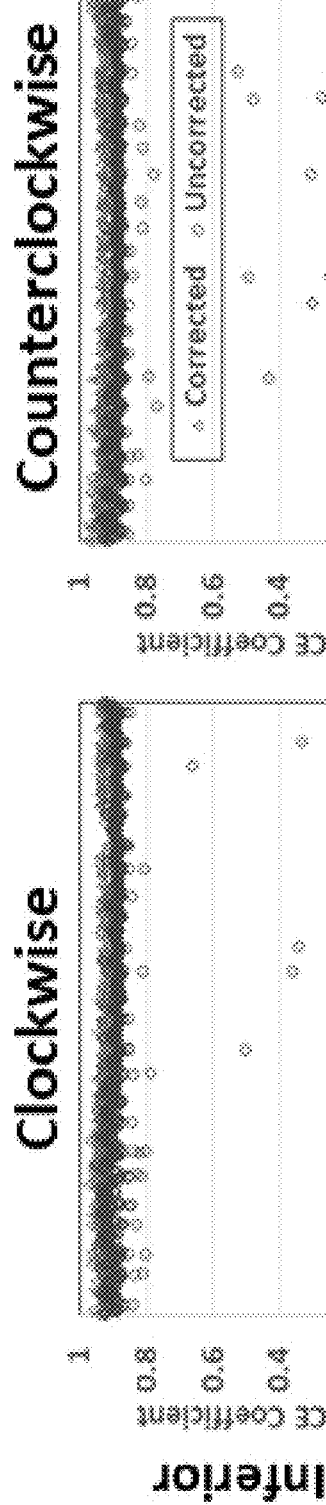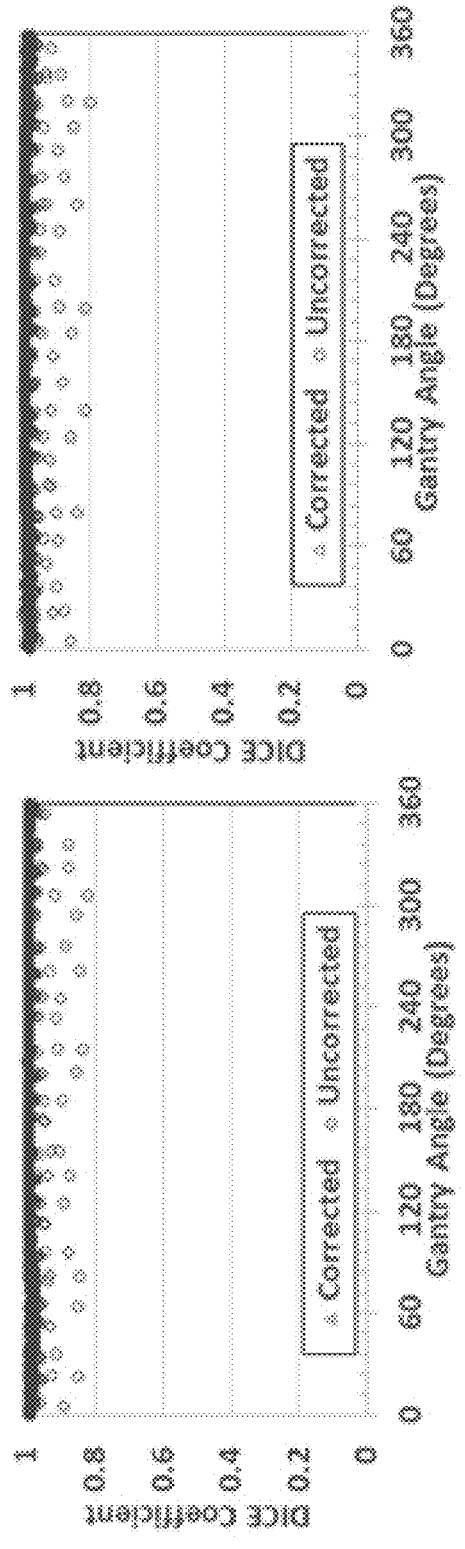
FIG. 10A  FIG. 10B  FIG. 10C  FIG. 10D

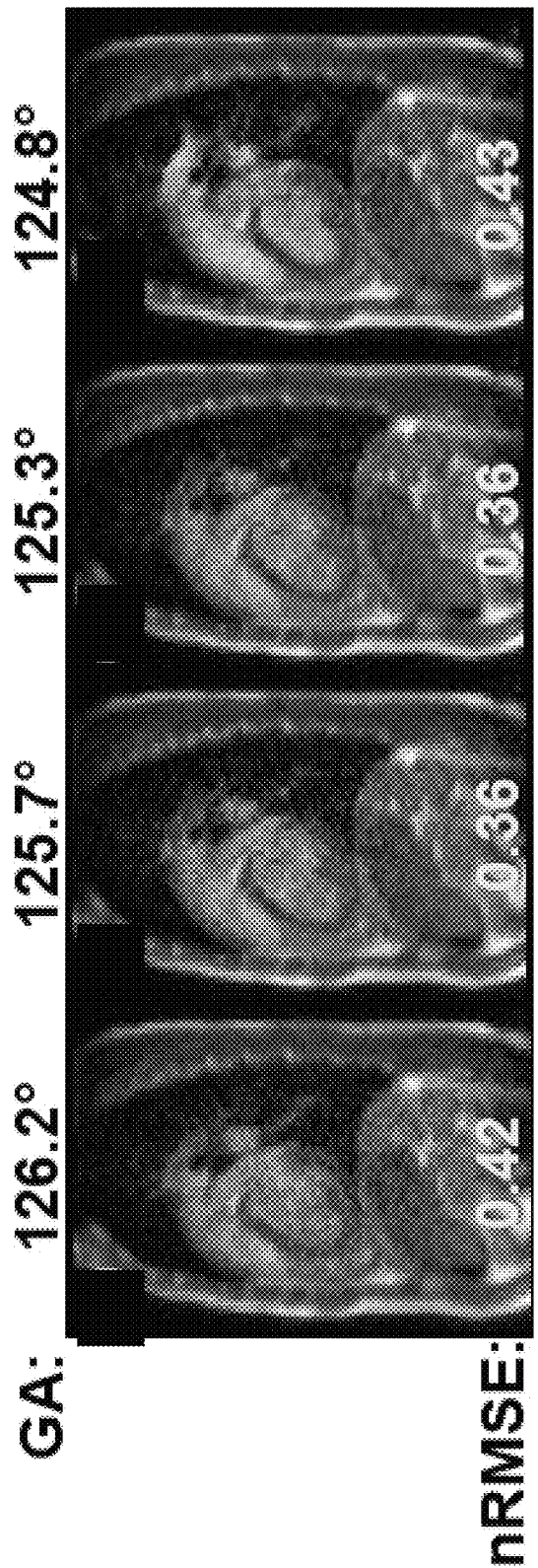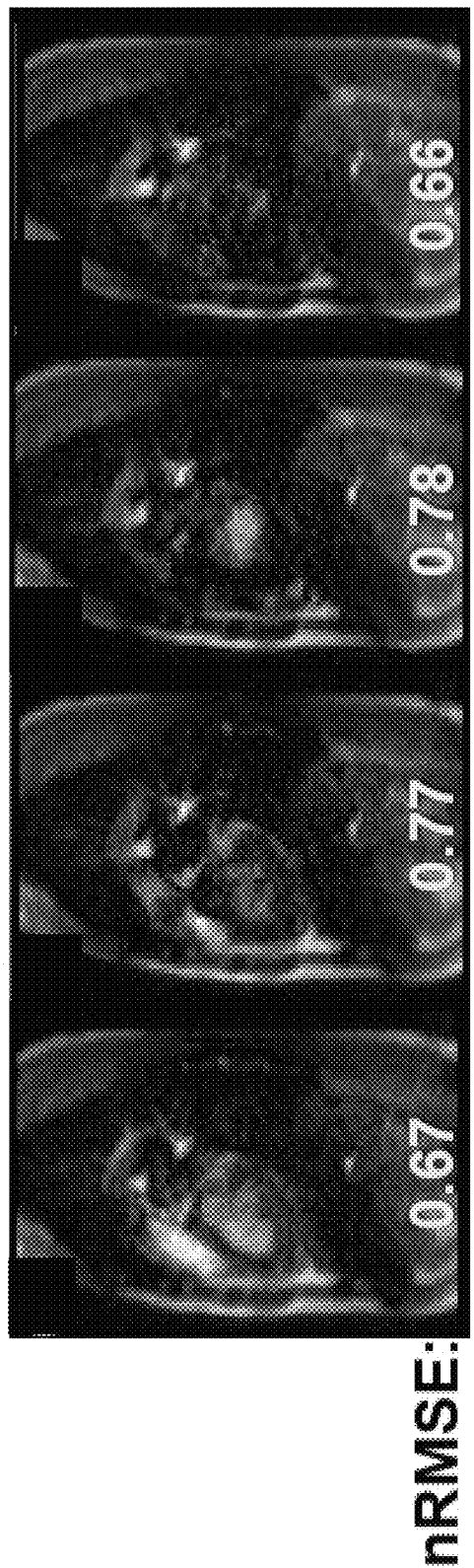

SYSTEMS AND METHODS FOR REAL-TIME B0 FLUCTUATION COMPENSATION

CROSS-REFERENCE TO RELATED APPLICATIONS

This application claims priority from U.S. Provisional Application Ser. No. 63/183,521 filed on May 3, 2021, which is incorporated herein by reference in its entirety.

STATEMENT REGARDING FEDERALLY SPONSORED RESEARCH OR DEVELOPMENT

This invention was made with government support under HL148210 awarded by the National Institutes of Health. The government has certain rights in the invention.

MATERIAL INCORPORATED-BY-REFERENCE

Not applicable

FIELD OF THE DISCLOSURE

The present disclosure generally relates to devices, systems, and methods for enhancing MRI image quality and tracking accuracy in MR-guided treatment systems.

BACKGROUND OF THE DISCLOSURE

Magnetic resonance imaging (MRI) guided radiation therapy (MR-IGRT) provides superior soft-tissue contrast versus x-ray based image guided radiation therapy (X-IGRT) at least in part due to the capability of MRI to more readily visualize and accurately demarcate the tumor. MR-IGRT enables real-time tumor tracking and beam gating during treatment without the additional imaging radiation dose associated with x-ray imaging. Real-time gating/tracking and daily treatment adaptation facilitates more aggressive hypo-fractionation and dose escalation while sparing organs at risk (OARs). Stereotactic MRI-guided online adaptive radiation therapy (SMART) with daily adaptive planning and real-time beam gating in combination with dose escalation has resulted in dramatic improvements in survival for unresectable pancreatic cancer.

One limitation of MR-IGRT is the long procedure time and associated impacts on patient throughput, cost, and access. Each adaptive MR-IGRT procedure can last two hours including setup, patient alignment, plan adaptation, and gated beam delivery. MR-IGRT treatments are currently restricted to Step-and-Shoot delivery for which the gantry and multi-leaf collimators (MLCs) are stationary at each treatment delivery phase, resulting in prolonged delivery time with multiple beam angles to implement high conformal tumor coverage. However, volumetric modulated arc therapy (VMAT), a therapy delivery method in which the gantry and MLC move during beam delivery, can reduce dose delivery times by as much as 75% while improving tumor coverage conformality (due to unlimited beam angles).

Unfortunately, VMAT techniques are currently precluded in MR-IGRT because of the confounding effects of time-dependent electromagnetic (EM) interference (EMI) between the MRI and linear accelerator (Linac) subsystems on MRI image quality and tracking accuracy. Existing MRI-Linac systems typically include a large volume of magnetic and radiofrequency shielding in their gantries. MRI-Linacs also have a split-bore with a >20 cm longitudinal gap centered at isocenter in their main magnetic field (B0) and gradient windings that allow increased coupling between the static and gradient magnetic fields and the gantry components. Sources of EMI in MR-IGRT may include: 1) EMI from static variations in the system configuration (e.g., gantry angle and MLC configuration); 2) EMI from moving metal elements during gantry rotation and MLC motion; and 3) EMI from thermal changes in ferromagnetic structures (e.g., Linac magnetic shielding and passive shims) during system operation and reconfiguration. The effects of EMI in MR-IGRT may include shifts in B0 center frequency, field homogeneity, and gradient and B0 eddy currents in the MRI subsystem that may result in image artifacts, geometric distortion, and imaging isocenter variations.

Artifact-free imaging during radiation therapy is an important step towards implementing arc therapy on MR-IGRT systems. Previous studies showed that MLC motion did not produce significant EMI that impacted MRI quality on the currently two FDA-approved commercial MRI-Linac models. However, large B0 fluctuations that can produce image artifacts and imaging isocenter shifts were reported for a commercial 0.35 T MRI-Linac during gantry rotation. These B0 fluctuations potentially constitute an obstacle to performing VMAT techniques in MR-IGRT.

Balanced steady-state free procession (bSSFP) sequences like true fast imaging with steady-state precession (True-FISP) or balanced fast field echo (bFFE) are typically used for real-time imaging during MR-IGRT treatment due to their high signal to noise ratio (SNR) and high temporal resolution. However, bSSFP sequences are sensitive to B0 fluctuations. Off-resonances of $\pm 1/(2*TR)$ where TR is the repetition time result in bands of signal loss known as null bands. Significant null bands have been previously reported during gantry rotation of a 0.35T MR-IGRT system. Null banding was primarily attributed to sinusoidal B0 fluctuations during gantry rotation due to the six gantry mounted ferromagnetic mu-metal buckets spaced every 60° that are typically included in commercial MRI-Linac models. Additionally, center frequency offsets can result in misalignment between the imaging and radiotherapy isocenters resulting in dosimetric errors. This misalignment presents as an errant shift in the object in the read-out direction. The magnitude of the misalignments is dictated by $\Delta f/rBW$ where $\Delta f$ is the center frequency offset associated with the B0 fluctuation and rBW is the receiver bandwidth.

Real-time prospective B0 corrections were previously demonstrated in other MR imaging applications, including free induction decay (FID) navigators used prospectively to correct B0 fluctuations. Small frequency shifts associated with diffusion weighted MRI were resolved by adjusting the RF pulse and receiver frequencies in real-time by calculating the center frequency shift from the phase correction lines acquired during the echo planar imaging (EPI) readout. External and internal field probes were also used to measure B0 fluctuations with the results fed back into a B0 correction coil or the pulse sequence. Typically, the various methods were designed for B0 fluctuations of <50 Hz. By contrast, gantry rotation B0 variations typically span a range of ±400 Hz, rendering existing prospective B0 corrections unsuitable for use in MR-IGRT.

SUMMARY

In one aspect, a method for obtaining high-quality MR images for guidance of a treatment using an MR-IGRT system is disclosed that includes, for each frame of a cine data MR data acquisition sequence: producing, using the MR-IGRT system, a non-selective RF excitation pulse; detecting, using the MR-IGRT system, a plurality of free induction decay (FID) signals; calculating a center frequency offset based on the plurality of free induction decay (FID) signals; modifying the image acquisition selective excitation RF pulses and receiver phase based on the center frequency offset; obtaining an MR image dataset using the modified image acquisition selective excitation RF pulses and receiver phase; and reconstructing a frame of the MR image, wherein the MR image comprises reduced EMI artifacts associated with gantry motion. In one aspect, the non-selective RF excitation pulse is selected from a rectangular excitation pulse, an apodized sinc pulse, or an adiabatic pulse. In one aspect, the non-selective RF excitation pulse is the rectangular excitation pulse with a duration of less than about 0.5 ms and a flip angle of no more than about 30°. In one aspect, the method further includes producing at least one magnetization restoration pulse prior to obtaining the MR image dataset using the modified image acquisition selective excitation RF pulses and receiver phase.

In one aspect, the center frequency offset $\Delta f$ is calculated using the equation:

$$\Delta f = \frac{1}{2\pi(N-k+1)} \sum_{k=k}^{N} \frac{d(\phi_{new,i} - \phi_{ref,i})}{dt}$$

where $\phi\_new$ is a most recent unaliased FID navigator phase, and $\phi\_ref$ is an unaliased reference FID navigator phase.

In one aspect, the transmitter/receiver phase of each imaging sequence is adjusted for each excitation using the equation: $\phi_n = (n-1) \cdot \Delta f \cdot TR \cdot 360° + \phi_{cycle}$, where $\Phi n$ is a phase increment in degrees for the nth excitation, TR is a repetition time, $\Delta f$ is a central frequency offset obtained from a previous measurement, and $\phi$cycle is a 0°/180° alternating phase.

DESCRIPTION OF THE DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIG. 10A is a graph of QUASAR phantom results summarizing Dice coefficients for the inferior contours during clockwise gantry rotation while acquiring 2D bSSFP MRIs at 7.3 fps. The B0 correction (Δ) resulted in consistent Dice coefficients compared to images acquired without real-time B0 correction (O).

FIG. 10B is a graph of QUASAR phantom results summarizing Dice coefficients for the inferior contours during counterclockwise gantry rotation while acquiring 2D bSSFP MRIs at 7.3 fps. The B0 correction (Δ) resulted in consistent Dice coefficients compared to images acquired without real-time B0 correction (O). The zero value at gantry angle 80° in (b) resulted from the tracking algorithm selecting the wrong contour.

FIG. 10C is a graph of QUASAR phantom results summarizing Dice coefficients for the superior contours during clockwise gantry rotation while acquiring 2D bSSFP MRIs at 7.3 fps. The B0 correction (Δ) resulted in consistent Dice coefficients compared to images acquired without real-time B0 correction (O).

FIG. 10D is a graph of QUASAR phantom results summarizing Dice coefficients for the superior contours during counterclockwise gantry rotation while acquiring 2D bSSFP MRIs at 7.3 fps. The B0 correction (Δ) resulted in consistent Dice coefficients compared to images acquired without real-time B0 correction (O).

FIG. 11A contains a first of four frames of Volunteer 1 (37-year old male) using the 2D Cartesian bSSFP sequence with (a-d) and without (e-h) real time B0 compensation while the radiation therapy gantry rotated counterclockwise from 126° to 125°. Significant null bands are present when B0 compensation was not used. GA: Gantry angle. nRMSE: Normalized root mean square error.

FIG. 11A contains a first of four frames of Volunteer 1 (37-year old male) using the 2D Cartesian bSSFP sequence with (a-d) and without (e-h) real time B0 compensation while the radiation therapy gantry rotated counterclockwise from 126° to 125°. Significant null bands are present when B0 compensation was not used. GA: Gantry angle. nRMSE: Normalized root mean square error.

FIG. 11A contains a first of four frames of Volunteer 1 (37-year old male) obtained using the 2D Cartesian bSSFP sequence with real time B0 compensation while the radiation therapy gantry rotated counterclockwise from 126° to 125°.GA: Gantry angle. nRMSE: Normalized root mean square error.

FIG. 11B contains a second of four frames of Volunteer 1 (37-year old male) obtained using the 2D Cartesian bSSFP sequence with real time B0 compensation while the radiation therapy gantry rotated counterclockwise from 126° to 125°. GA: Gantry angle. nRMSE: Normalized root mean square error.

FIG. 11C contains a third of four frames of Volunteer 1 (37-year old male) obtained using the 2D Cartesian bSSFP sequence with real time B0 compensation while the radiation therapy gantry rotated counterclockwise from 126° to 125°. GA: Gantry angle. nRMSE: Normalized root mean square error.

FIG. 11D contains a fourth of four frames of Volunteer 1 (37-year old male) obtained using the 2D Cartesian bSSFP sequence with real time B0 compensation while the radiation therapy gantry rotated counterclockwise from 126° to 125°. GA: Gantry angle. nRMSE: Normalized root mean square error FIG. 11E contains the image of FIG. 11A without real time B0 compensation.

FIG. 11F contains the image of FIG. 11B without real time B0 compensation.

FIG. 11G contains the image of FIG. 11C without real time B0 compensation.

FIG. 11H contains the image of FIG. 11D without real time B0 compensation.

Figure 1:
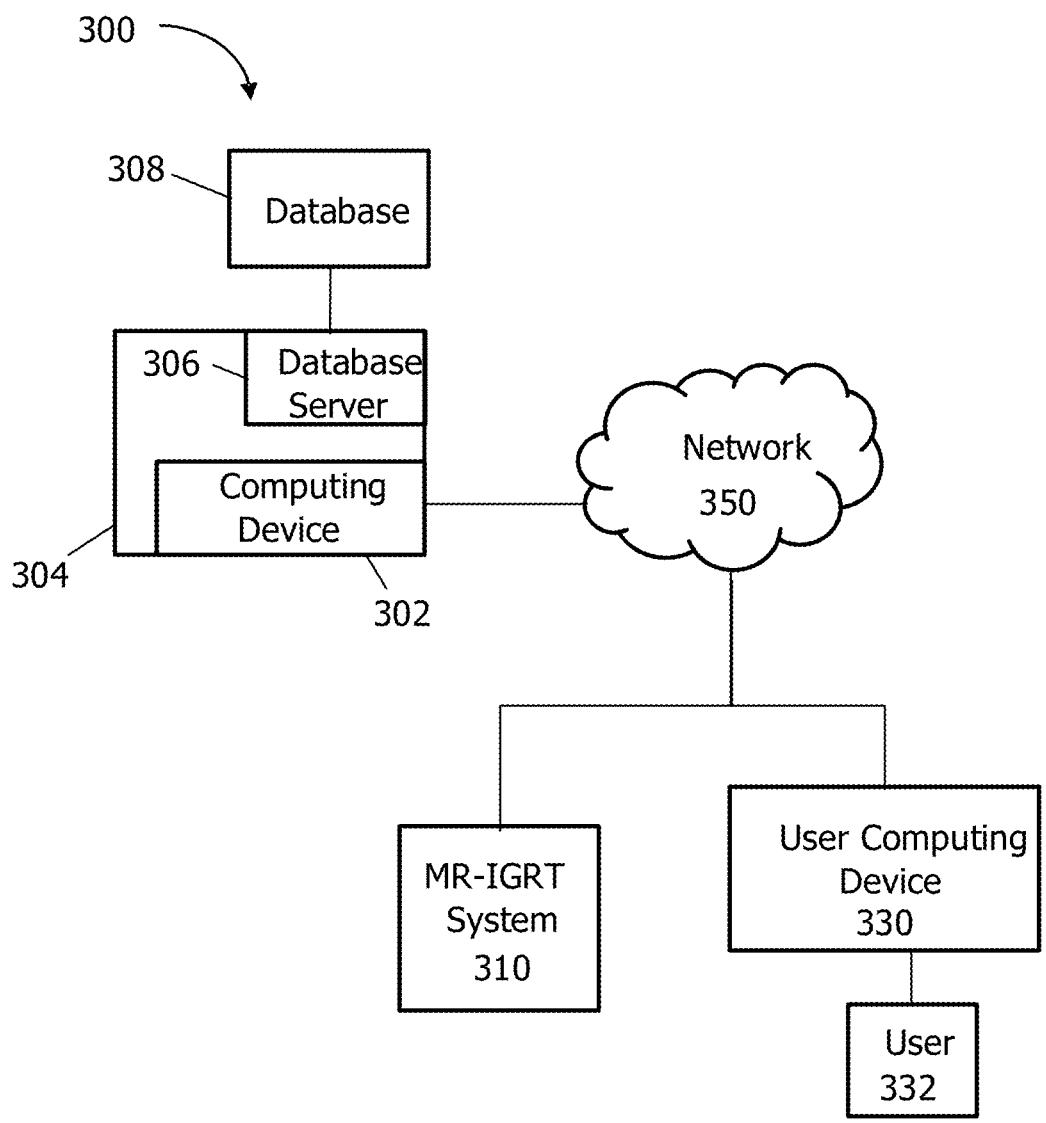
FIG. 1 is a block diagram schematically illustrating a system in accordance with one aspect of the disclosure.

There are shown in the drawings arrangements that are presently discussed, it being understood, however, that the present embodiments are not limited to the precise arrangements and are instrumentalities shown. While multiple embodiments are disclosed, still other embodiments of the present disclosure will become apparent to those skilled in the art from the following detailed description, which shows and describes illustrative aspects of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION OF THE INVENTION

In various aspects, devices, systems, and methods for enhancing MRI image quality and tracking accuracy in an MR-guided treatment system subject to time-varying electromagnetic interference between the MRI subsystem and the treatment subsystem are disclosed. In various aspects, the disclosed devices, systems and methods effectuate one or more corrections to reduce the impact of EMI on MR signals obtained during an MR-guided therapy including, but not limited to, magnetic resonance imaging (MRI) guided radiation therapy (MR-IGRT). In various other aspects, the disclosed devices, systems and methods further effectuate one or more retrospective corrections to reduce the various effects of EMI on MR image quality. In some aspects FID navigators, described in additional detail herein, are used to prospectively (in real time) correct center frequency offsets of ±400 Hz and minimize image variations and artifacts due to gantry rotation on a low-field MRI-Linac device.

Figure 16:
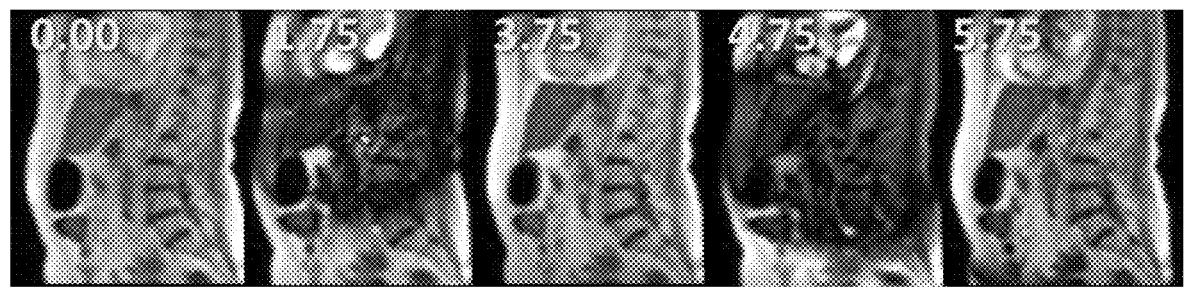
FIG. 16 contains a series of MR images with EMI artifacts associated with gantry rotation from 3000 to 3200 in 76-year old patient receiving adaptive MR-IGRT on the 0.35 T MRI-Linac. Time labels are in seconds. 2D sagittal bSSFP cine: TE/TR: 0.91/2.10, Flip angle: 60°, GRAPPA: 2, 3.5× 3.5×7 mm, 1351 Hz/pixel, 2 averages, 4 frames/s
Figure 17:
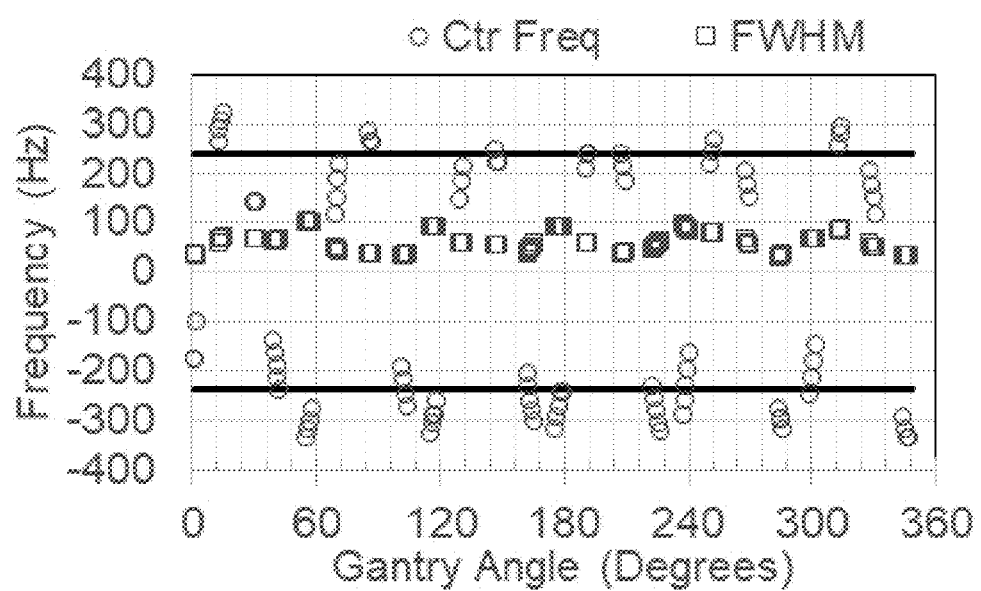
FIG. 17 is a graph summarizing center frequency offsets and field inhomogeneities (FWHM) over a range of gantry angles corresponding to severe artifacts during this sequence and continuous gantry rotation measured in a phantom. Horizontal black lines correspond to ±1/(2·TR).

EMI artifacts associated with gantry movements associated with adaptive MR-IGRT treatments degrade the accuracy and effectiveness of such treatments. By way of non-limiting example, FIG. 16 contains a series of MR images containing EMI artifacts and FIG. 17 is a graph summarizing the center frequency offsets, field inhomogeneities (FWHM), and gantry angle associated with these severe artifacts within MR images obtained during adaptive MR-IGRT.

In various aspects, the EMI artifacts associated with gantry rotation during magnetic resonance imaging (MRI) guided radiation therapy (MR-IGRT) using volumetric modulated arc therapy (VMAT) delivery methods using FID navigators integrated into a pulse sequence used for image acquisition during MR-IGRT. The modified pulse sequence includes an RF pulse configured to generate free induction decay (FID) followed by FID acquisition. As described in additional detail below, the measured FID is used to calculate a center frequency offset that is provided as feedback used to modify the imaging pulse sequence to compensate for image artifacts associated with gantry rotation.

Figure 5:
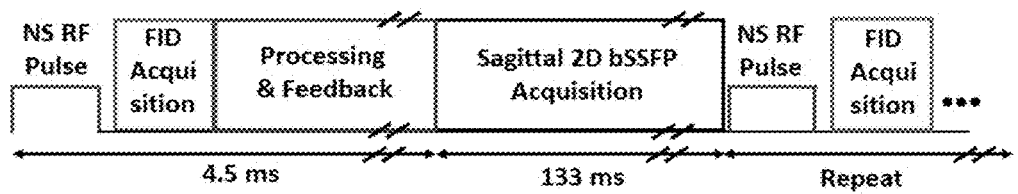
FIG. 5 is a schematic illustration of TrueFISP with non-selective FID navigator. The FID navigator is run before each image acquisition. A nonselective (hard) pulse generates an FID from which the center frequency offset is measured and fed back to the pulse sequence for real-time correction of successive selective excitations and receiver frequencies. Each bSSFP acquisition includes a steady-state preparation consisting of variable flip angle excitations. The gradients in the steady-state preparation dephase the FID to avoid interference with the image quality.

FIG. 5 is a schematic illustration showing a modified pulse sequence in one aspect. As illustrated in FIG. 5, a FID navigator employing a nonselective (rectangular) RF excitation pulse (Flip angle: 35°, RF duration: 500 μs, acquisition dwell time: 8 μs, 64 complex points) was integrated into a 2D Cartesian bSSFP (TrueFISP) cine sequence (Table I) to measure center frequency fluctuations. A delay of 100 μs was added after each navigator RF pulse and prior to the free induction decay (FID) acquisition to protect the receiver from RF coil ring-down. The frequency shift obtained using the first FID navigator serves as the center frequency reference used for subsequent frequency shift calculations as described below. Each subsequent FID navigator is used to estimate the center frequency offset according to the following equation:

$$\Delta f = \frac{1}{2\pi(N-k+1)} \sum_{i=k}^{N} \frac{d(\phi_{new,i} - \phi_{ref,i})}{dt} \qquad \text{Eqn. (1)}$$

where $\phi_{new}$ is the most recent unaliased FID navigator phase, and $\phi_{ref}$ is the unaliased reference FID navigator phase. In some aspects, the first nine and last ten sampled ADC points from each FID navigator were discarded to reduce variance (k=10 and N=54).

TABLE I

Comparison of TrueFISP pulse sequence parameters.

| Parameter | Pulse Sequence | | |
|---|---|---|---|
| | FID Navigator Cartesian | ViewRay Cartesian | ViewRay Radials |
| Frame rate (fps) | 7.3 | 4 | 8* |
| Field of view (mm) | 350 | 350 | 350 |
| Voxel size (mm³) | 3.5 × 3.5 × 7 | 3.5 × 3.5 × 7 | 2.43 × 2.43 × 7 |
| Number of Phase Encodes/Radials | 100 | 100 | 144 |

TABLE I-continued

Comparison of TrueFISP pulse sequence parameters.

| Parameter | Pulse Sequence | | |
| --- | --- | --- | --- |
| | FID Navigator Cartesian | ViewRay Cartesian | ViewRay Radials |
| Number of slices | 1 | 1 | 1 |
| Number of averages | 1 | 2 | 1 |
| Echo time (ms) | 1.09 | 0.91** | 1.38 |
| Repetition time (ms) | 2.18 | 2.10 | 3.47 (500)† |
| Receiver bandwidth (Hz/pixel) | 1515 | 1515 | 890 |
| Partial Fourier | 75% | 75% | 100% |
| GRAPPA | 2 | 2 | 1 |

*Using ¼ k-space view sharing.
**Asymmetric echo.
†The TR for the radial acquisition is defined to include the full k-space acquisition time.
fps: frames per second.

In various aspects, the image acquisition selective excitation RF pulses and receiver phase are adjusted based on the center frequency offset measured using the FID navigator. In some aspects, if a bSSFP imaging sequence is used, transmitter/receiver phase of each imaging sequence is adjusted for each excitation as expressed in Eqn. (2):

$$\phi_n = (n-1) \cdot \Delta f \cdot TR \cdot 360° + \phi_{cycle} \qquad \text{Eqn. (2)}$$

where $\Phi_n$ gives the phase increment in degrees for the nth excitation, TR is the repetition time, and $\Delta f$ is the central frequency offset obtained from the previous navigator measurement. $\phi_{cycle}$ is the 0°/180° alternating phase typical in bSSFP sequences.

Figure 13:
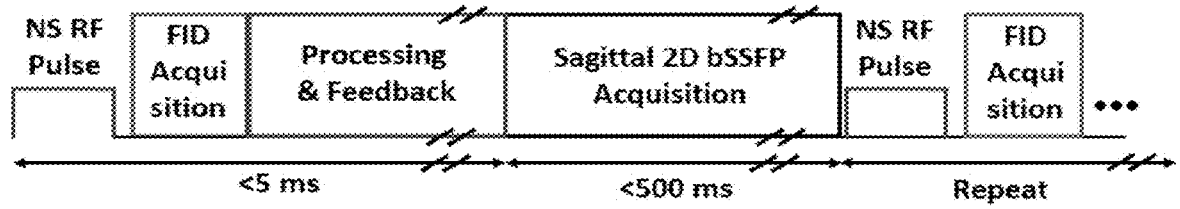
FIG. 13 is a schematic illustration of an FID navigator that includes a short duration (e.g., 0.5 ms) nonselective (NS) RF pulse (flip angle ≤30°) followed by a short readout and then processed to obtain the center frequency offset. 2D SSFP acquisition times may range from 125 ms (Cartesian) to 500 ms (view-shared radials) to enable frame rates of 8 frames per second (fps). Higher frame rates can be achieved using sparse sampling (e.g., golden angle radials) and machine learning reconstructions.

In some aspects, the FID navigator is executed without a gradient readout to minimize the effects of off-resonance due to tissue motion. In one aspect, the FID navigator includes a nonselective "hard" pulse as illustrated in FIG. 13. In one aspect, the nonselective "hard" pulse is a short duration nonselective (NS) RF pulse with a duration of less than about 0.5 ms and a flip angle of no more than about 30°. In other aspects, a shaped (e.g., apodized sinc) pulse or an adiabatic pulse can be substituted for the non-selective hard pulse in the FID navigator.

Figure 14:
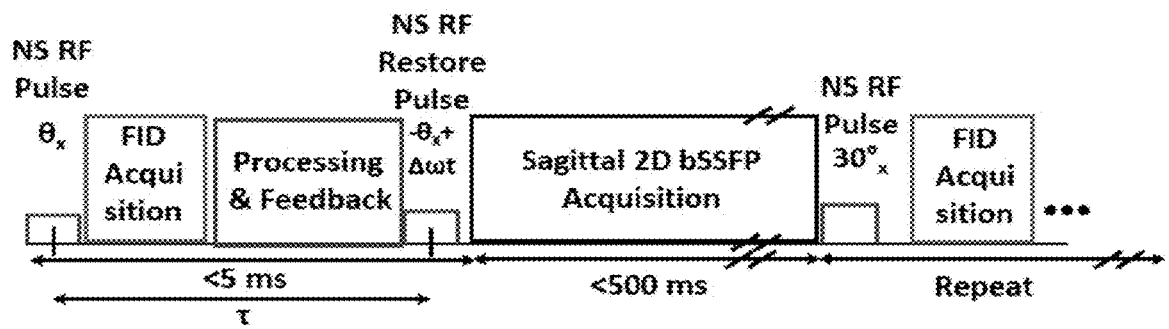
FIG. 14 is a schematic illustration of an FID navigator that includes a phase-tracking magnetization restoration pulse.
Figure 15:
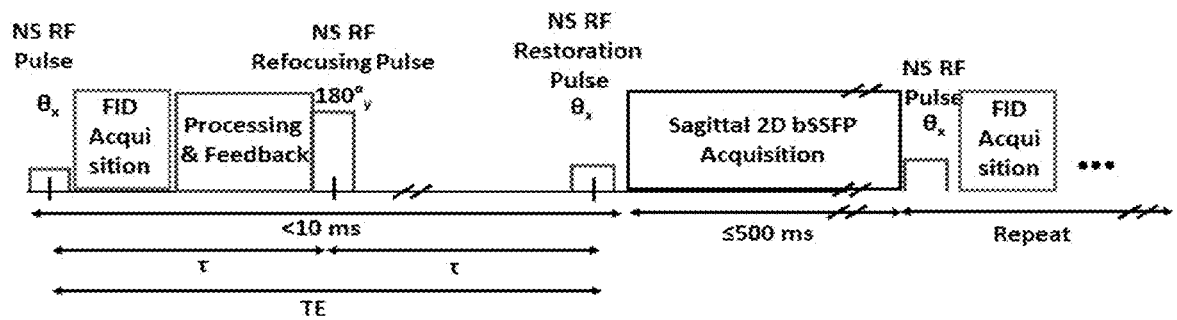
FIG. 15 is a schematic illustration of an FID navigator that includes a phase-tracking spin echo magnetization restoration pulse. The 180° and θ transmitter phases are adjusted based on the center frequency offset measured by the FID navigator.

In other aspects, the modified pulse sequence that includes the FID navigator may include at least one magnetization restoration pulse delivered after processing of the FID signals and communication of the center frequency shift feedback to the imaging sequence. A modified pulse sequence that includes one magnetization restoration pulse and multiple magnetization restoration pulses are shown in FIGS. 14 and 15. Without being limited to any particular theory, the magnetization restoration pulses are used to minimize imaging signal-to-noise ratios (SNRs) losses due to the FID navigator magnetization used to measure center frequency shifts.

In various aspects, FID data analysis and real-time feedback of the center frequency offset to the pulse sequence currently takes several milliseconds on a Siemens VB architecture, although short processing times may be achievable using additional system architectures. In other aspects, 2D SSFP acquisition times used for image acquisition may range from about 125 ms (Cartesian) to about 500 ms (view-shared radials), resulting in imaging frame rates of about 8 frames per second (fps). In additional aspects, higher frame rates may be achieved using sparse sampling (e.g., golden angle radials) and machine learning reconstructions.

In various aspects, the one or more prospective corrections may include real-time compensation of EMI. In some aspects, the prospective correction may include modifications of the MR scanner's pulse sequence execution based on gantry kinematics and the predicted EMI associated with the gantry kinematics. In these aspects, the gantry kinematics may be calculated within the pulse sequence. Non-limiting examples of gantry kinematics calculated within the pulse sequence include the gantry's position, velocity, and acceleration.

In various aspects, the EMI associated with the gantry kinematics may be predicted using a numerical modeling of EMI during gantry rotation and image formation. In one aspect, an in silico EM model may be constructed based on CAD data describing the relative positions of EMI-inducing elements of the MRI-Linac system, as well as experimental measurements of EMI phenomena during the execution of one or more pulse sequences associated with MR-IGRT. In various aspects, the high-fidelity predictive numerical simulations of EMI due to gantry kinematics that are produced using the EM model described above may be used for both prospective corrections to data acquisition and for retrospective image reconstruction algorithms as described herein.

In some aspects, primary pulse sequences used during real-time tracking and beam gating associated with MR-IGRT include radial and Cartesian bSSFP sequences. By way of non-limiting example, radial and Cartesian bSSFP sequences may be modified to incorporate dynamic field compensation based on the kinematics and the EM modeling results obtained as described above. In some aspects, the modified pulse sequence may calculate and adjust the center frequency and gradient shims in real-time. Center frequency adjustments (A00) may be made to the RF excitation and receiver acquisition. Dynamic gradient shimming (A10, A11, and B11) may be made using a dynamic shimming functionality of the MR scanner configured to modify shimming based on gantry kinematics and EM modeling results.

Non-limiting examples of aspects of MR image quality that may be reduced using the prospective corrections include B0 center frequency shifts, field homogeneities, and gradient and B0 eddy currents.

In various aspects, the retrospective corrections described above may reduce at least one or more effects of EMI on MR image quality including, but not limited to, EM model-based compensation of B0 fluctuations during image reconstruction. In various aspects, the retrospective corrections may reduce the effects of EMI on one or more aspects of MR image quality including, but not limited to, image artifacts, geometric distortion, and imaging isocenter variations.

Non-limiting examples of suitable methods of retrospective corrections include model-based image reconstruction methods using an approximated signal model and real-time deep learning (DL)-based reconstruction methods.

In some aspects, the retrospective corrections may make use of a high-fidelity computational model of the MRI image formation process for the MR-guided treatment system including, but not limited to, the MR-IGRT (MRI-Linac) system. The image formation process in the presence of magnetic field fluctuations and inhomogeneities associated with EMI may be produced by integrating the EM model described above with an MRI simulator including, but not limited to MRILab. The MRI simulator is configured to simulate various aspects of MR imaging including, but not limited to, MRI signal formation, k-space acquisition, and MRI image reconstruction. Digital phantoms (virtual objects) in MRILab are defined as 3D maps of spin densities and relaxations times ($T_1$, $T_2$, $T_2^*$). Dynamic phantoms may be defined in MRILab by defining 3D motion trajectories to the digital phantoms. In some aspects, MRILab may be used to solve the Bloch equations to simulate k-space measurements from the digital phantom, and a reconstruction method including, but not limited to, inverse FFT may be used to reconstruct images. In various aspects, the high-fidelity computational model of the MRI image formation process may be validated by comparing simulated MR images to reference digital images.

In various aspects, the EM model-based compensation of B0 fluctuations during image reconstruction may be implemented using a k-space model that represents the spatiotemporal fluctuations of the magnetic field due to EMI induced by the rotating gantry. The k-space model may include a representation of a k-space signal $s(t_i)$ in the presence of magnetic field inhomogeneity and off-resonance $(\Delta\omega(r, t_i))$ given by:

$$s(t_i) = H_{\Delta\omega} f(r, t_i) + \eta_i = \int c(r) f(r, t_i) e^{-i\Delta\omega(r, t_i)} e^{-i2\pi k(t_i) \cdot r} dr + \eta_i,$$

where f (r, $t_i$) is the sought-after dynamic image at location r and time $t_i$, c(r) is the coil sensitivity, k($t_i$) is the k-space trajectory, and $\eta_i$ represents the measurement error.

By way of non-limiting example, the EMI model described above may be used to construct 120 off-resonance maps corresponding to equispaced rotation angles of the gantry for a fixed rotation velocity. Uncertainty in the estimates and discrepancies between the signal model $H_{\Delta\omega} f$ and reality may be accounted for by use of the BAE framework. In BAE, the reconstructed image is the maximum a posteriori estimator $f^* = \text{argmax}_f \pi_{like}(s|f) \pi_{pr}(f)$, where the likelihood $\pi_{like}(s|f)$ is the probability of observing the signal s given the image f, and $\pi_{pr}(f)$ is a properly chosen image prior (such as Gaussian random field, or total variation prior). The likelihood function $\pi_{like}$ (s|f) is defined by use of an enchanted error model $s(t_i) = H_{\Delta\omega} f(r, t_i) + \eta_i + \epsilon_i$, with modeling error $\epsilon_i$. For each gantry rotation angle (120 equispaced angles), the mean and covariance matrix of the error model are estimated by comparing the signal model $s(t_i) = H_{\Delta\omega} f(r, t_i)$ with the output of the Bloch equation based high-fidelity model. Under the assumption of a Gaussian distribution (a common ansatz in BAE), estimating $f^*$ reduces to a standard penalized least squares minimization, where the discrepancy terms $s(t_i) - H_{\Delta\omega} f(r, t_i)$ are properly weighted by the model error covariance. A look-up map may be constructed to select the imaging operator and modeling error statistics to use in the model-based reconstruction for each rotation angle of the gantry.

In various aspects, the retrospective corrections may be real-time deep learning (DL)-based reconstruction methods including, but not limited to, a modified iFFT direct inversion method developed by the use of machine learning. The DL reconstruction methods will be trained in two steps. DL methods will be first trained using pairs of numerical phantoms and corresponding simulated k-space data. The DL methods may be tailored to a specific MR-IGRT system, including, but not limited to, a ViewRay MRIdian system, by retraining the DL layers closer to the input and output of the network by use of the in vivo data sets. This technique, known as transfer learning[66], will allow us to leverage simulated data sets to learn physical invariants (embedded in the inner layers of the network) and in vivo data sets to account for system parameters. In the proposed framework, we will learn 120 mappings (corresponding to equispaced gantry rotation angles for a fixed rotation speed) from the simulated or in vivo subsampled k-space data to dense off-resonance-compensated k-space data, from which an image is obtained using iFFT. A U-Net architecture will be used to accomplish the two-fold task of: 1) Inferring missing k-space information; and 2) Compensating for inhomogeneity and fluctuations in the magnetic field.

In some aspects, the disclosed devices, systems, and methods reduce the effects of time-dependent electromagnetic (EM) interference (EMI) between the MRI and linear accelerator (Linac) subsystems of an MRI-guided radiation therapy (MR-IGRT) system, resulting in MRI image quality and tracking accuracy that is sufficient to support the use of volumetric modulated arc therapy (VMAT) techniques in MR-IGRT that were previously precluded due to insufficient MR image quality and tracking accuracy.

As illustrated in the Examples below, the feasibility of using FID navigators to correct center frequency offsets and minimize the effects of gantry rotation on image quality in a phantom and in vivo was demonstrated. The B0 compensation generally resulted in improved image quality as indicated by a reduction in nRMSE and an increase in Dice coefficient.

In various aspects, the use of FID navigators as described herein reduces artifacts associated with gantry movement, but also may decrease SNR and may decrease imaging duty cycle. In some aspects, the use of the FID navigator sequence may result in half of the SNR as compared to similar sequences without the FIR navigator. Bloch equation simulations indicate that the reduction in bSSFP magnetization in the liver from the FID navigator may be less than about 20%. In some aspects, a magnetization restoration pulse may be added after the FID navigator acquisition to enhance SNR, as illustrated in FIGS. 14 and 15. In other aspects, SNR may be increased by using long-term averaging and a slower frame rate for data acquisition. By way of non-limiting example, ViewRay's 4 fps Cartesian uses short-term averaging on the MRI-Linac to minimize artifacts from B0 eddy currents. In some aspects, the FID navigator may be less compatible with short-term averaging for which the k-space data is acquired contiguously. In long-term averaging, the k-space data acquisition is broken into single-shot packets that enable frequent execution of the FID navigator.

In some aspects, the bSSFP sequence can be modified to add or redirect one of the readouts for use as a B0 navigator while preserving the steady-state free precession. As disclosed herein, nonselective excitation (see FIG. 13) was used in the data acquisition sequence to maximize the SNR and precision of the center frequency offset measurement due to the challenges of low field (0.35 T). In other aspects, the addition of the FID navigator may slightly reduce the image acquisition duty cycle. In some aspects, when one FID navigator is acquired per k-space acquisition resulting in a 3% drop in acquisition duty cycle for the Cartesian acquisitions.

Figure 22:
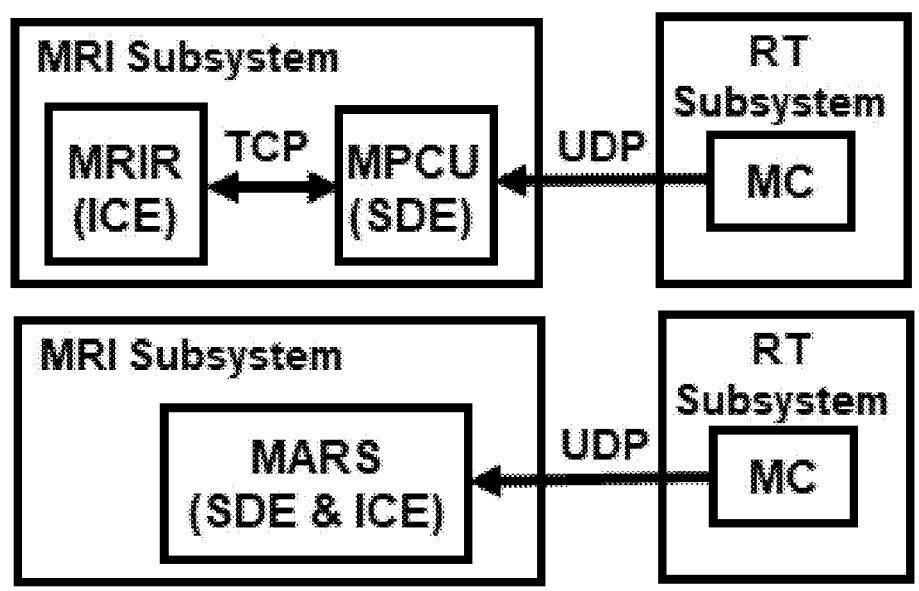
FIG. 22 is a block diagram illustrating the arrangement of elements of a magnetic resonance imaging (MRI) guided radiation therapy (MR-IGRT) system. The gantry position is broadcast from the motion controller (MC) to the measurement and physiology control unit (MPCU) of the MRI over a UDP interface. The gantry kinematics can be transmitted to the MR image reconstruction (MRIR) via their TCP interface. After the MRI upgrade, the measurement and reconstruction system (MARS) will receive the gantry data.
Figure 23:
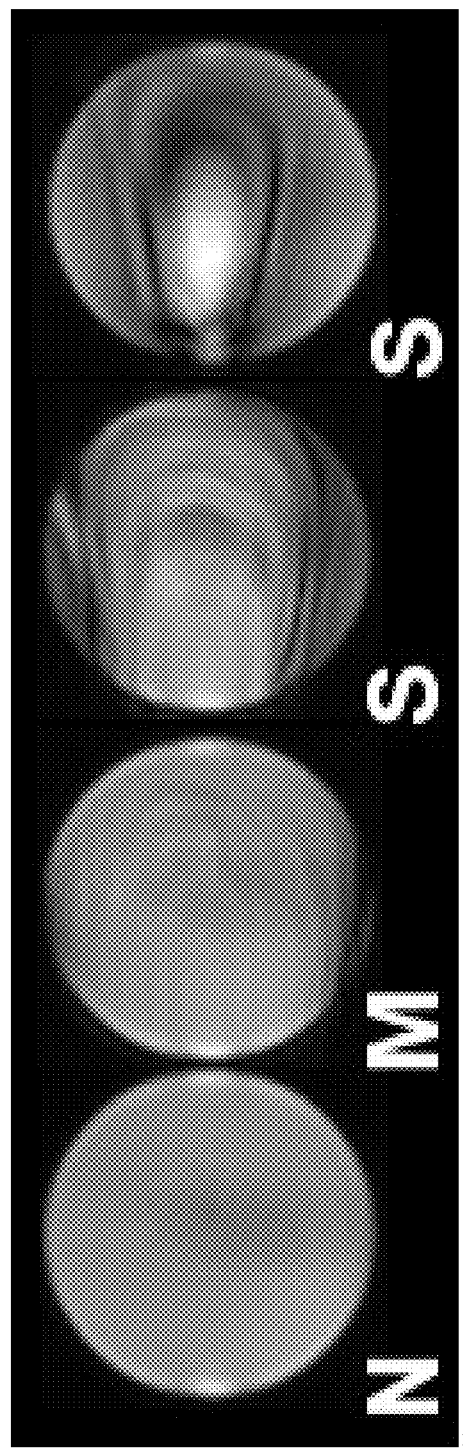
FIG. 23 is a series of images illustrating artifact grading during gantry rotation obtained during 2D sagittal cine Cartesian bSSFP MRI in 24 cm DSV phantom. N: No significant artifact; M: Minor artifact (small effect on tracking); S: Severe artifact (interferes with tracking).
Figure 24:
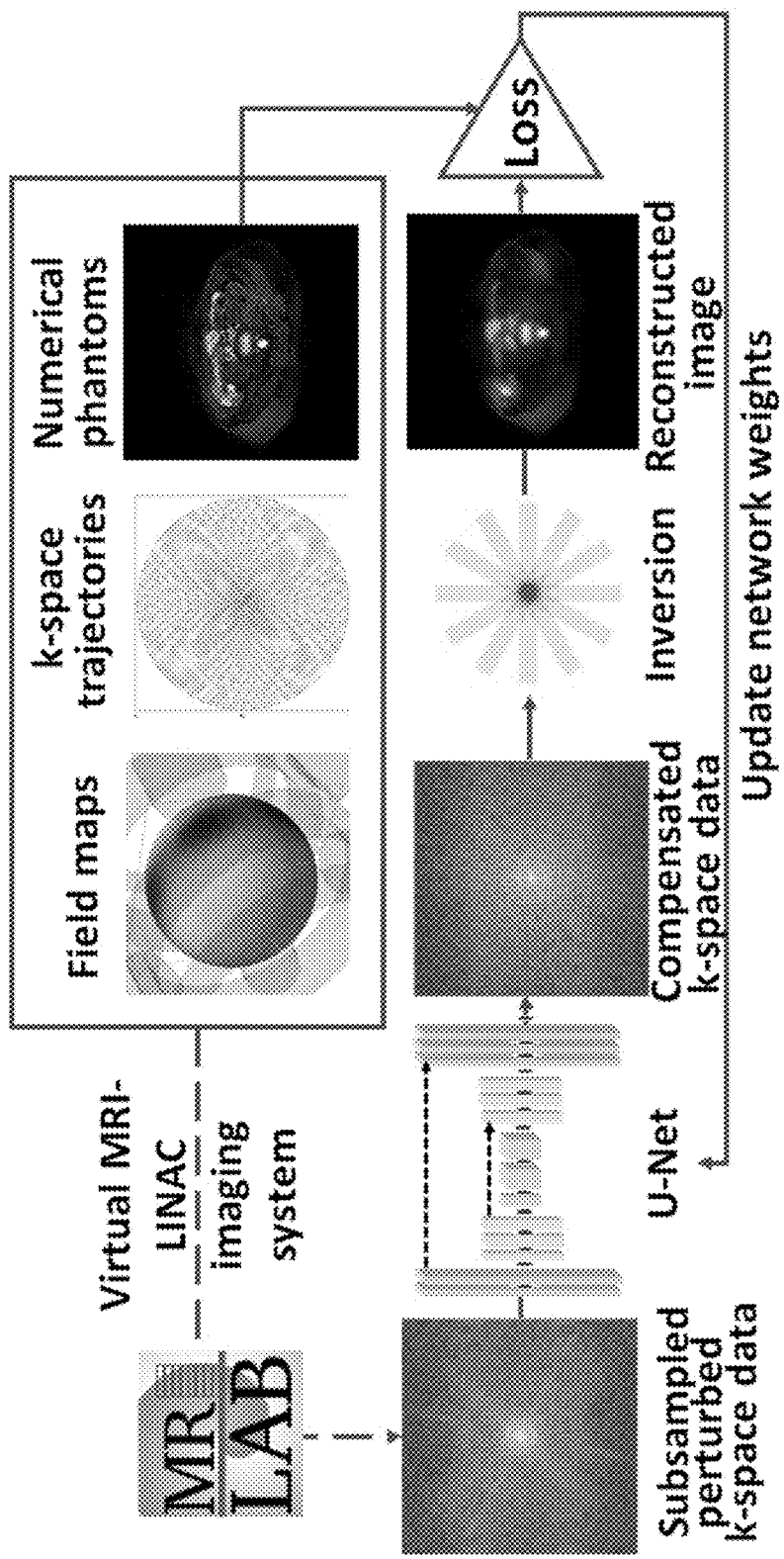
FIG. 24 is a schematic diagram illustrating the training and use of a supervised learning framework configured to minimize EMI artifacts.

In some aspects, an alternative to the use of FID navigators is to change the transmitter and receiver frequencies in real time based on the gantry's position and velocity. By way of non-limiting example, the pulse sequence architecture of the ViewRay MRI-Linac permits dynamic updates to the transmitter and receiver phases and the first order (gradient) shims. As illustrated in FIG. 22, the MRI-Linac sends each Step and Shoot gantry position from the motion controller to the pulse sequence over a user datagram protocol (UDP) interface to enable B0 and first order shim corrections while the gantry is stationary. The B0 and gradient shim corrections may be implemented based on a look-up table derived from spherical phantom measurements of off-resonance and field homogeneities performed with a stationary gantry. In some aspects, the UDP interface may be used to communicate the real-time gantry position and velocity back to the pulse sequence as feedback to adjust each imaging sequence based on the gantry movement and position.

As described in the examples, significant differences in center frequency were measured between the spherical phantom and in vivo during gantry rotation. Consequently, a look-up table or model-based solution for minimizing off-resonance during rotating gantry may be unsatisfactory unless the corrected center frequency offset can be maintained within ±1/(4*TR). As discussed in the examples, the maximum variation between measured offsets was 102 Hz which is less than 1/(4*TR) (i.e., 115 Hz).

In various other aspects, an NMR field probe or camera may be integrate into the system architecture and the data acquired by the NMR field probes or camera may be used as feedback to modify the imaging sequence to compensate for the EMI effects due to gantry movements. Without being limited to any particular theory, the NMR field probe is capable of acquiring data at a high sampling rate, but the field probe makes use of separate transmitter and receiver electronics, and must be electromagnetically decoupled from the MRI and Linac. In some aspects, the center frequency data measured by the NMR field probes or camera may be fed back to the MRI pulse sequence using the UDP interface in a manner similar to that described above (see FIG. 22).

In various aspects, uncorrected B0 offsets during readout gradients may cause imaging isocenter shifts depending on the receiver bandwidth. Based on previous measurements, uncorrected B0 offsets from gantry rotation combined with the typical 2D bSSFP cine sequences used for treatment (rBW>850 Hz/pixel) may result in imaging isocenter shifts of less than half a pixel whereas deep respiration (55 mm displacements) along the readout direction can produce localized frequency offsets of >20 kHz. For sequences (e.g., T1 or T2 weighted) with receiver bandwidths comparable to the B0 offsets, the imaging isocenter shifts may exceed the limits for radiation therapy (2 mm) or stereotactic radiosurgery (1 mm).

Translating the FID navigator technique as described herein to radial TrueFISP acquisitions may be modified to accommodate the long acquisition window (0.5 s). Eddy currents have been were previously calculated from, and corrections were applied to, the radial k-space spokes. In some aspects, k-space spokes may be repurposed to serve as an FID navigator or additional navigator spokes may be added to serve as an FID navigator.

In various aspects, self-navigation derives motion or B0 offsets from the k-space data. Self-navigation was previously demonstrated for retrospective 3D image reconstruction on the MRIdian. A consistency navigator was previously demonstrated to measure rapid changes in B0 from the k-space data of gradient recalled echo scans.

As previously mentioned, distinguishing center frequency offsets from respiratory motion using a navigator with a readout gradient may be challenging since sagittal cines have the readout parallel to the principal direction of motion. Changing the readout axis of the navigator may still result in motion-related frequency offsets in the kHz.37

In various aspects, the B0 compensation using the FID navigator as disclosed herein does not address changes in field homogeneity due to the rotating gantry. However, as demonstrated in the Examples, field homogeneity was weakly affected by a moving versus a stationary gantry. Currently, the MRIdian operates with neither fixed nor dynamic gradient shimming.

As demonstrated in the Examples, center frequency offsets induced by the rotation of the ferromagnetic gantry resulted in image quality degradation while using 2D Cartesian bSSFP cine sequences. Dynamic B0 compensation using a FID navigator improved image quality albeit with a 3% drop in acquisition duty cycle and a <20% drop in SNR.

Computing Systems and Devices

FIG. 1 depicts a simplified block diagram of a computing device 300 for implementing the methods described herein. As illustrated in FIG. 1, the computing device 300 may be configured to implement at least a portion of the tasks associated with the disclosed method using the MR-IGRT system 310 including, but not limited to: operating the MR-IGRT system 310 to obtain MR images using one or more prospective corrections and reconstructing the MR images using one or more retrospective corrections as described herein. The computer system 300 may include a computing device 302. In one aspect, the computing device 302 is part of a server system 304, which also includes a database server 306. The computing device 302 is in communication with a database 308 through the database server 306. The computing device 302 is communicably coupled to the MR-IGRT system 310 and a user computing device 330 through a network 350. The network 350 may be any network that allows local area or wide area communication between the devices. For example, the network 350 may allow communicative coupling to the Internet through at least one of many interfaces including, but not limited to, at least one of a network, such as the Internet, a local area network (LAN), a wide area network (WAN), an integrated services digital network (ISDN), a dial-up-connection, a digital subscriber line (DSL), a cellular phone connection, and a cable modem. The user computing device 330 may be any device capable of accessing the Internet including, but not limited to, a desktop computer, a laptop computer, a personal digital assistant (PDA), a cellular phone, a smartphone, a tablet, a phablet, wearable electronics, smartwatch, or other web-based connectable equipment or mobile devices.

Figure 2:
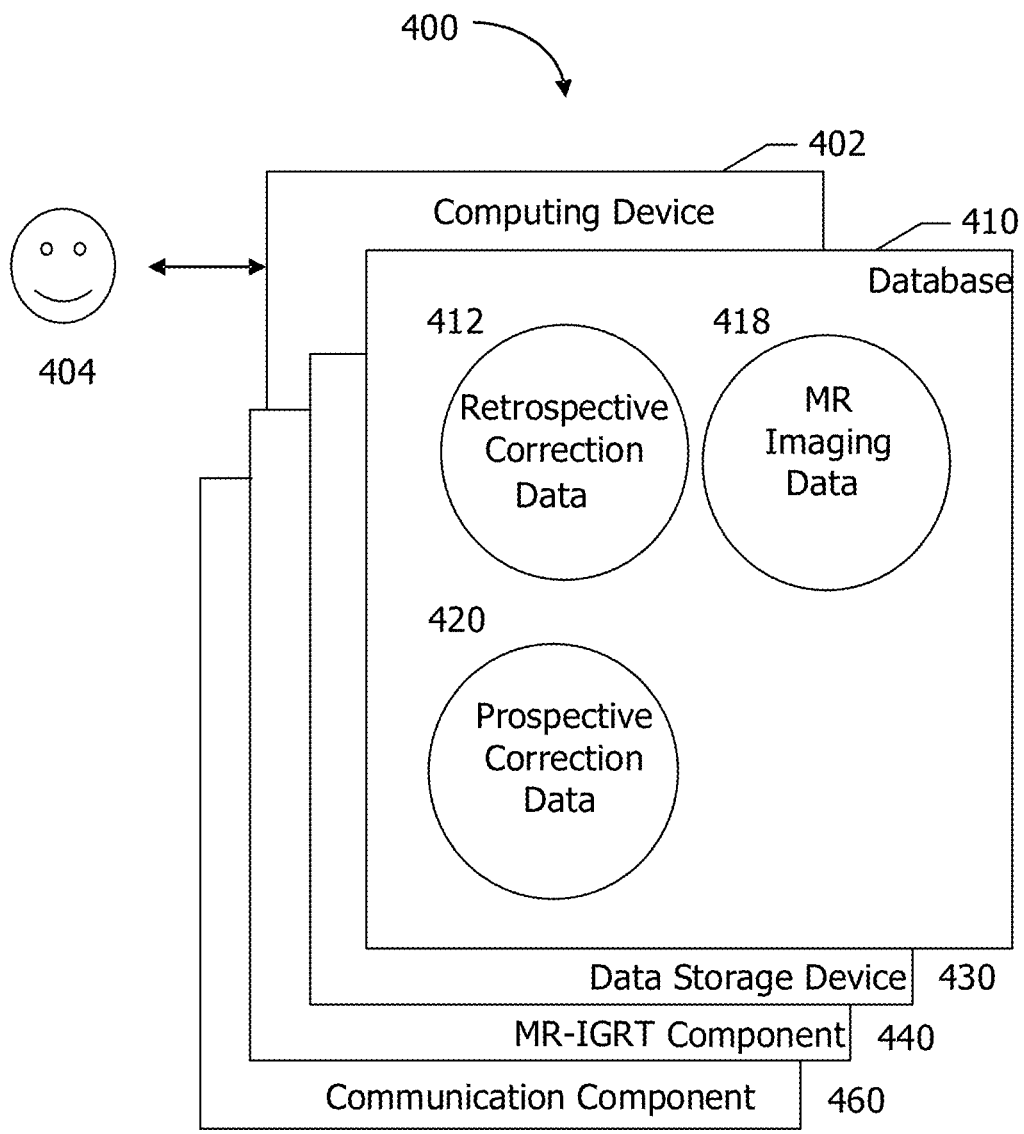
FIG. 2 is a block diagram schematically illustrating a computing device in accordance with one aspect of the disclosure.

In other aspects, the computing device 302 is configured to perform a plurality of tasks associated with obtaining high-quality MR images using at least one or more prospective corrections and one or more retrospective corrections as described herein. FIG. 2 depicts a component configuration 400 of computing device 402, which includes database 410 along with other related computing components. In some aspects, computing device 402 is similar to computing device 302 (shown in FIG. 1). A user 404 may access components of computing device 402. In some aspects, database 410 is similar to database 308 (shown in FIG. 1).

In one aspect, database 410 includes MR imaging data 418, prospective correction data 420, and retrospective correction data 412. Non-limiting examples of suitable prospective correction data 420 include any values of parameters defining the EMI model or modifications of the MR pulse sequences based on the EM model. In one aspect, the retrospective correction data 412 may include reconstruction model-based parameters or deep learning model parameters used in a method of reconstructing PET images as described herein.

Computing device 402 also includes a number of components that perform specific tasks. In the exemplary aspect, computing device 402 includes a data storage device 430, MR-IGRT component 440, and communication component 460. Data storage device 430 is configured to store data received or generated by computing device 402, such as any of the data stored in database 410 or any outputs of processes implemented by any component of computing device 402. MR-IGRT component 440 is configured to obtain high quality MR images using the prospective and retrospective corrections for EMI effects using the methods described herein in various aspects.

Communication component 460 is configured to enable communications between computing device 402 and other devices (e.g. user computing device 330 and MR-IGRT system 310, shown in FIG. 1) over a network, such as network 350 (shown in FIG. 1), or a plurality of network connections using predefined network protocols such as TCP/IP (Transmission Control Protocol/Internet Protocol).

Figure 3:
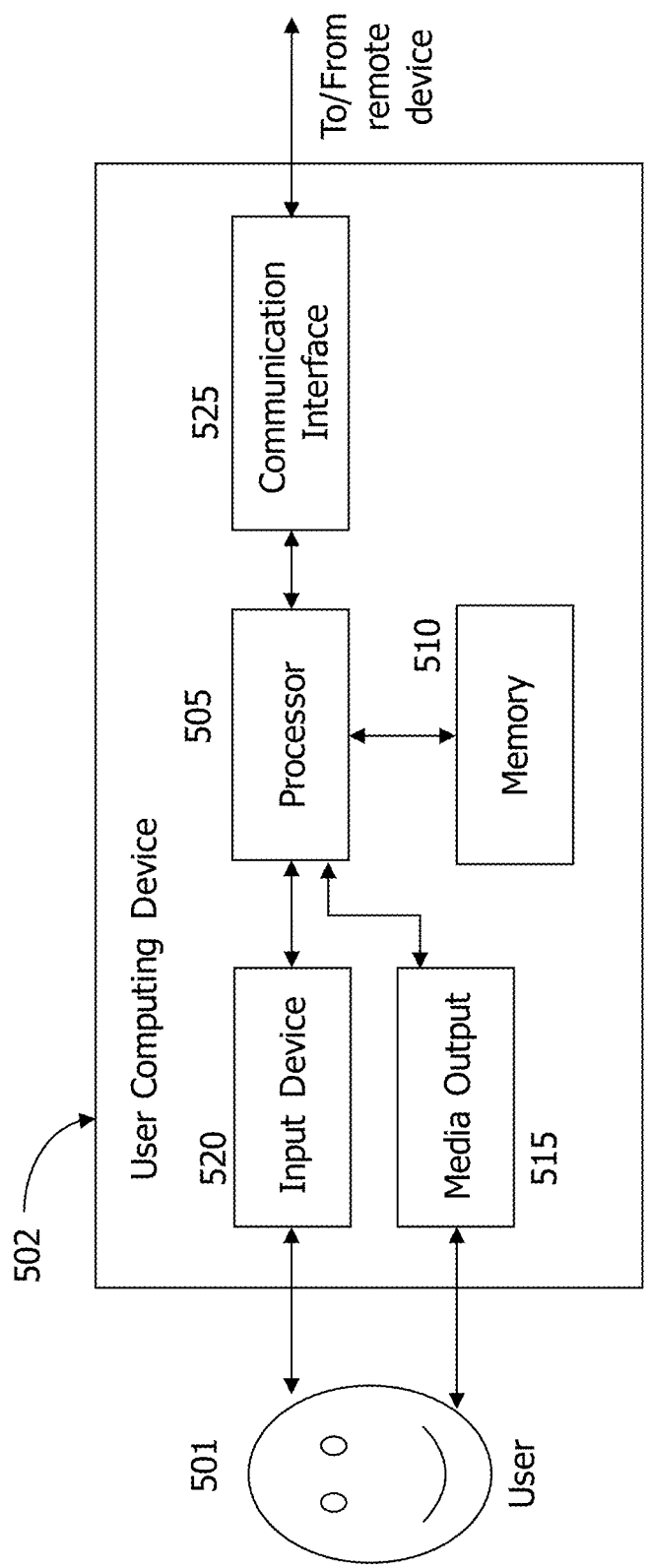
FIG. 3 is a block diagram schematically illustrating a remote or user computing device in accordance with one aspect of the disclosure.

FIG. 3 depicts a configuration of a remote or user computing device 502, such as user computing device 330 (shown in FIG. 1). Computing device 502 may include a processor 505 for executing instructions. In some aspects, executable instructions may be stored in a memory area 510. Processor 505 may include one or more processing units (e.g., in a multi-core configuration). Memory area 510 may be any device allowing information such as executable instructions and/or other data to be stored and retrieved. Memory area 510 may include one or more computer-readable media.

Computing device 502 may also include at least one media output component 515 for presenting information to a user 501. Media output component 515 may be any component capable of conveying information to user 501. In some aspects, media output component 515 may include an output adapter, such as a video adapter and/or an audio adapter. An output adapter may be operatively coupled to processor 505 and operatively coupleable to an output device such as a display device (e.g., a liquid crystal display (LCD), organic light emitting diode (OLED) display, cathode ray tube (CRT), or "electronic ink" display) or an audio output device (e.g., a speaker or headphones). In some aspects, media output component 515 may be configured to present an interactive user interface (e.g., a web browser or client application) to user 501.

In some aspects, computing device 502 may include an input device 520 for receiving input from user 501. Input device 520 may include, for example, a keyboard, a pointing device, a mouse, a stylus, a touch sensitive panel (e.g., a touchpad or a touch screen), a camera, a gyroscope, an accelerometer, a position detector, and/or an audio input device. A single component such as a touch screen may function as both an output device of media output component 515 and input device 520.

Computing device 502 may also include a communication interface 525, which may be communicatively coupleable to a remote device. Communication interface 525 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in memory area 510 are, for example, computer-readable instructions for providing a user interface to user 501 via media output component 515 and, optionally, receiving and processing input from input device 520. A user interface may include, among other possibilities, a web browser and client application. Web browsers enable users 501 to display and interact with media and other information typically embedded on a web page or a website from a web server. A client application allows users 501 to interact with a server application associated with, for example, a vendor or business.

Figure 4:
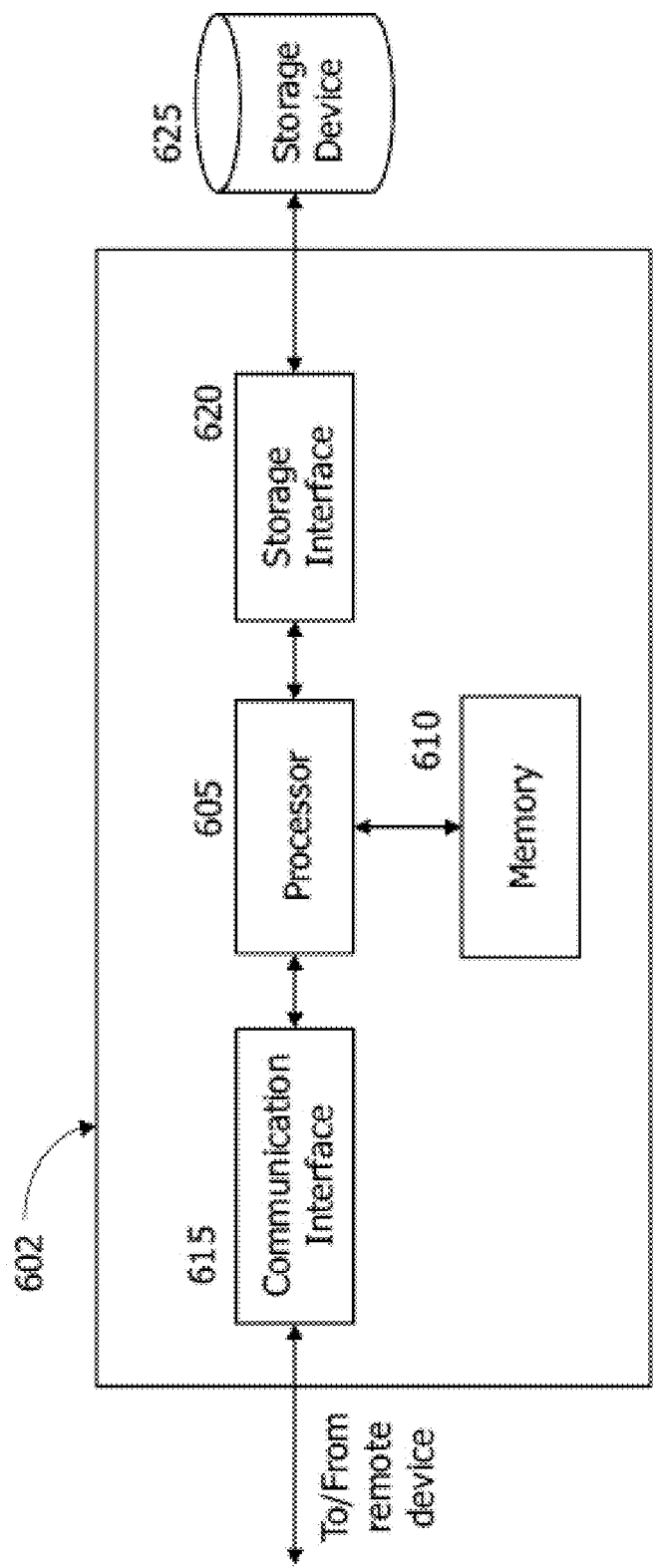
FIG. 4 is a block diagram schematically illustrating a server system in accordance with one aspect of the disclosure.

FIG. 4 illustrates an example configuration of a server system 602. Server system 602 may include, but is not limited to, database server 306 and computing device 302 (both shown in FIG. 1). In some aspects, server system 602 is similar to server system 304 (shown in FIG. 1). Server system 602 may include a processor 605 for executing instructions. Instructions may be stored in a memory area 625, for example. Processor 605 may include one or more processing units (e.g., in a multi-core configuration).

Processor 605 may be operatively coupled to a communication interface 615 such that server system 602 may be capable of communicating with a remote device such as user computing device 330 (shown in FIG. 1) or another server system 602. For example, communication interface 615 may receive requests from a user computing device 330 via a network 350 (shown in FIG. 1).

Processor 605 may also be operatively coupled to a storage device 625. Storage device 625 may be any computer-operated hardware suitable for storing and/or retrieving data. In some aspects, storage device 625 may be integrated in server system 602. For example, server system 602 may include one or more hard disk drives as storage device 625. In other aspects, storage device 625 may be external to server system 602 and may be accessed by a plurality of server systems 602. For example, storage device 625 may include multiple storage units such as hard disks or solid state disks in a redundant array of inexpensive disks (RAID) configuration. Storage device 625 may include a storage area network (SAN) and/or a network attached storage (NAS) system.

In some aspects, processor 605 may be operatively coupled to storage device 625 via a storage interface 620. Storage interface 620 may be any component capable of providing processor 605 with access to storage device 625. Storage interface 620 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 605 with access to storage device 625.

Memory areas 510 (shown in FIG. 3) and 610 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are examples only and are thus not limiting as to the types of memory usable for the storage of a computer program.

The computer systems and computer-implemented methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local or remote processors, transceivers, servers, and/or sensors (such as processors, transceivers, servers, and/or sensors mounted on vehicle or mobile devices, or associated with smart infrastructure or remote servers), and/or via computer executable instructions stored on non-transitory computer-readable media or medium.

In some aspects, a computing device is configured to implement machine learning, such that the computing device "learns" to analyze, organize, and/or process data without being explicitly programmed. Machine learning may be implemented through machine learning (ML) methods and algorithms. In one aspect, a machine learning (ML) module is configured to implement ML methods and algorithms. In some aspects, ML methods and algorithms are applied to data inputs and generate machine learning (ML) outputs. Data inputs may include but are not limited to: images or frames of a video, object characteristics, and object categorizations. Data inputs may further include: sensor data, image data, video data, telematics data, authentication data, authorization data, security data, mobile device data, geolocation information, transaction data, personal identification data, financial data, usage data, weather pattern data, "big data" sets, and/or user preference data. ML outputs may include but are not limited to: a tracked shape output, categorization of an object, categorization of a type of motion, a diagnosis based on the motion of an object, motion analysis of an object, and trained model parameters ML outputs may further include: speech recognition, image or video recognition, medical diagnoses, statistical or financial models, autonomous vehicle decision-making models, robotics behavior modeling, fraud detection analysis, user recommendations and personalization, game AI, skill acquisition, targeted marketing, big data visualization, weather forecasting, and/or information extracted about a computer device, a user, a home, a vehicle, or a party of a transaction. In some aspects, data inputs may include certain ML outputs.

In some aspects, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, dimensionality reduction, and support vector machines. In various aspects, the implemented ML methods and algorithms are directed toward at least one of a plurality of categorizations of machine learning, such as supervised learning, unsupervised learning, and reinforcement learning.

In one aspect, ML methods and algorithms are directed toward supervised learning, which involves identifying patterns in existing data to make predictions about subsequently received data. Specifically, ML methods and algorithms directed toward supervised learning are "trained" through training data, which includes example inputs and associated example outputs. Based on the training data, the ML methods and algorithms may generate a predictive function that maps outputs to inputs and utilize the predictive function to generate ML outputs based on data inputs. The example inputs and example outputs of the training data may include any of the data inputs or ML outputs described above.

In another aspect, ML methods and algorithms are directed toward unsupervised learning, which involves finding meaningful relationships in unorganized data. Unlike supervised learning, unsupervised learning does not involve user-initiated training based on example inputs with associated outputs. Rather, in unsupervised learning, unlabeled data, which may be any combination of data inputs and/or ML outputs as described above, is organized according to an algorithm-determined relationship.

In yet another aspect, ML methods and algorithms are directed toward reinforcement learning, which involves optimizing outputs based on feedback from a reward signal. Specifically, ML methods and algorithms directed toward reinforcement learning may receive a user-defined reward signal definition, receive data input, utilize a decision-making model to generate an ML output based on the data input, receive a reward signal based on the reward signal definition and the ML output, and alter the decision-making model to receive a stronger reward signal for subsequently generated ML outputs. The reward signal definition may be based on any of the data inputs or ML outputs described above. In one aspect, an ML module implements reinforcement learning in a user recommendation application. The ML module may utilize a decision-making model to generate a ranked list of options based on user information received from the user and may further receive selection data based on a user selection of one of the ranked options. A reward signal may be generated based on comparing the selection data to the ranking of the selected option. The ML module may update the decision-making model such that subsequently generated rankings more accurately predict a user selection.

As will be appreciated based upon the foregoing specification, the above-described aspects of the disclosure may be implemented using computer programming or engineering techniques including computer software, firmware, hardware, or any combination or subset thereof. Any such resulting program, having computer-readable code means, may be embodied or provided within one or more computer-readable media, thereby making a computer program product, i.e., an article of manufacture, according to the discussed aspects of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are examples only, and are thus not intended to limit in any way the definition and/or meaning of the term "processor."

As used herein, the terms "software" and "firmware" are interchangeable and include any computer program stored in memory for execution by a processor, including RAM memory, ROM memory, EPROM memory, EEPROM memory, and non-volatile RAM (NVRAM) memory. The above memory types are examples only and are thus not limiting as to the types of memory usable for the storage of a computer program.

In one aspect, a computer program is provided, and the program is embodied on a computer readable medium. In one aspect, the system is executed on a single computer system, without requiring a connection to a server computer. In a further aspect, the system is being run in a Windows® environment (Windows is a registered trademark of Microsoft Corporation, Redmond, Washington). In yet another aspect, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some aspects, the system includes multiple components distributed among a plurality of computing devices. One or more components may be in the form of computer-executable instructions embodied in a computer-readable medium. The systems and processes are not limited to the specific aspects described herein. In addition, components of each system and each process can be practiced independently and separate from other components and processes described herein. Each component and process can also be used in combination with other assembly packages and processes. The present aspects may enhance the functionality and functioning of computers and/or computer systems.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Any publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following examples illustrate various aspects of the disclosure.

Example 1: Correction of EMI-Related B0 Field Variations on a Phantom

To demonstrate the feasibility of using FID navigators to correct center frequency offsets and minimize the effects of gantry rotation on image quality in a phantom, the following experiments were conducted.

All experiments were performed on a 0.35 T MRI-Linac (ViewRay MRIdian, Oakwood Village, OH) running software version 2.0.2. The MRI subsystem ran Siemens IDEA/ICE version VB19 software for pulse sequence execution and image reconstruction. All scans were performed using the MRI-Linac's "MRI QA" mode to allow for the use of modified pulse sequences and ICE real time feedback objects. Scans were acquired using two 6-channel flexible torso coils. Shimming was performed prior to each gantry rotation for all scans.

An QUASAR™ MRI4D motion phantom (ModusQA, London, Ontario) was imaged without motion using the 2D bSSFP cine sequence (see Table 1 above) with and without B0 compensation. Images were acquired with the gantry rotating fully clockwise (33°→90°→180°→270°→0°→30°), and with the gantry rotating fully counterclockwise (30°→0°→270°→180°→90°→33°). The gantry excluded travel to 31° or 32° by design so the above rotations represented the entire range of allowable gantry angles. The gantry rotation speed was previously measured at 3.42°/s (0.060 rad/s). FID navigators were acquired for images with and without B0 compensation and the center frequency offsets were calculated as described above (see Eqn. (1)). The frequency offsets determined for the images without B0 compensation were used to retrospectively align the cine frames for comparison with the cine frames using real-time B0 compensation.

Figure 6:
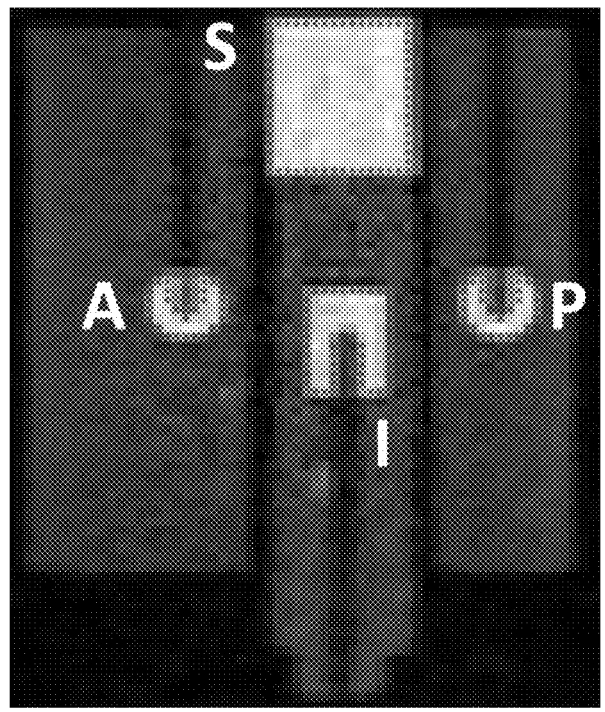
FIG. 6 contains a sagittal TrueFISP MRI (7.3 fps) of stationary QUASAR phantom with manually drawn reference contours shown in red on each of the anterior (A), superior (S), inferior (I), and posterior (P) targets.

The target tracking feature on the MRI-Linac was only available in RT mode using unmodified pulse sequences and reconstructions. To simulate tracking, the four MRI targets in the CIRS phantom were manually contoured on the first cine image of each acquisition retrospectively in MATLAB version R2019a (see FIG. 6) and an active contouring algorithm was applied to each subsequent frame using the manually drawn contour as the initial template. Dice coefficients between each active contour and the corresponding initial manual contour were calculated for the B0 corrected and uncorrected images acquired during gantry rotation. A Dice coefficient ≥0.7 ensured satisfactory similarity and the threshold was used as a surrogate for tracking performance. For each frame, the normalized root mean square error (nRMSE) was calculated for a region of interest (ROI) encompassing the phantom using the mean from a reference image acquired before gantry rotation. Paired t-tests between measurements with and without B0 compensation were conducted for the Dice coefficients and nRMSEs.

As a comparison, a computational model was used to estimate the center frequency offsets associated with gantry motion-related EMI effects. Based on Faraday's law, the center frequency offset should be directly proportional to the velocity of the gantry with a caveat: long time constant eddy currents produced center frequency offsets after the gantry came to rest. Therefore, the gantry rotation related center frequency offsets measured in the QUASAR phantom were modeled based on the convolution of a sinusoid input function (s) and a long time constant eddy current ($\tau$) transfer function (m) using Eqns. (3)-(5):

$$s(t) = \left(A \cdot \left(\frac{\omega}{|\omega_{max}|}\right) \cdot \text{Sin}[6\omega t + B + \theta_0]\right)(u[t_{start}] - u[t_{start} - t_{end}]) + C \quad \text{Eqn. (3)}$$

$$m(t) = \text{Exp}[-t/\tau]u[t] \quad \text{Eqn. (4)}$$

$$\Delta f(t) = s(t) \otimes m(t) \quad \text{Eqn. (5)}$$

where A, B, and C are fitting coefficients, $\omega$ is the gantry angular velocity with the maximum $\omega_{max}$ (currently 0.060 rad/s for the MRIdian), $\theta_0$ is the starting angle for the gantry rotation, u represents the unit step function with gantry rotation start and end times $t_{start}$ and $t_{end}$. Note that all parameters depend on the gantry rotation direction.

Figure 7A:
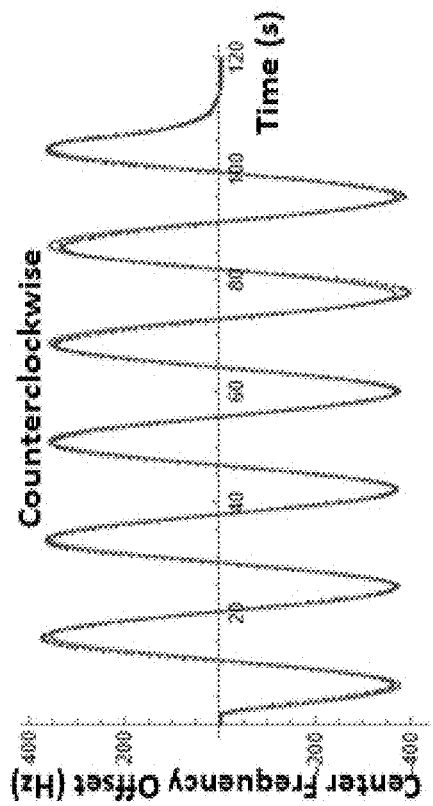
FIG. 7A is a graph of center frequency offsets (red points) versus time measured in the QUASAR phantom during clockwise gantry rotation. The blue lines represent the model in Eqs. (3-5). Note that the alignment of the model and data is imperfect because we assumed a constant gantry velocity (v=vmax) thus ignoring the gantry acceleration and deceleration at the initial and final gantry angles. The sinusoidal behavior is related to the six ferrous shield buckets mounted at 60° increments around the gantry.
Figure 7B:
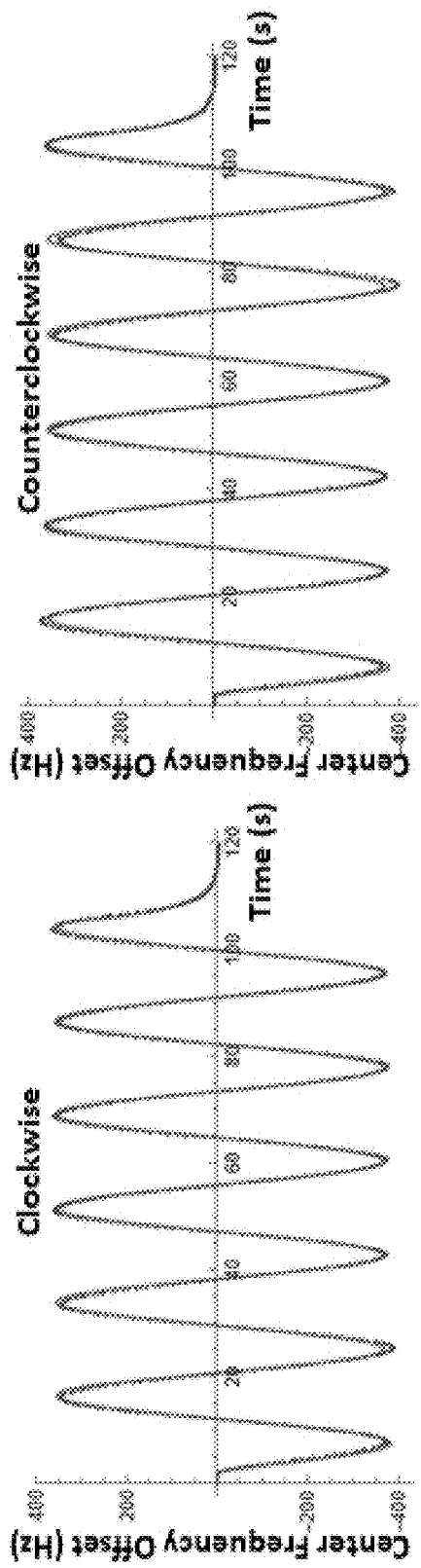
FIG. 7B is a graph of center frequency offsets (red points) versus time measured in the QUASAR phantom during counterclockwise gantry rotation.

FIGS. 7A and 7B summarize the center frequency offsets measured as a function of time during clockwise (FIG. 7A) and counterclockwise (FIG. 7B) gantry rotation in the QUASAR phantom and compares the data to the convolution model Eqns. (3-5). For clockwise rotation, the fit values were A=−197.530 Hz, B=−0.972 rad, C=−2.840 Hz, $\tau$=2.438 s, $\omega$=0.060 rad/s. For counterclockwise rotation, the fit values were A=213.964 Hz, B=−0.221 rad, C=−2.718 Hz, $\tau$=2.146, $\omega$=−0.060 rad/s.

Figure 8A:
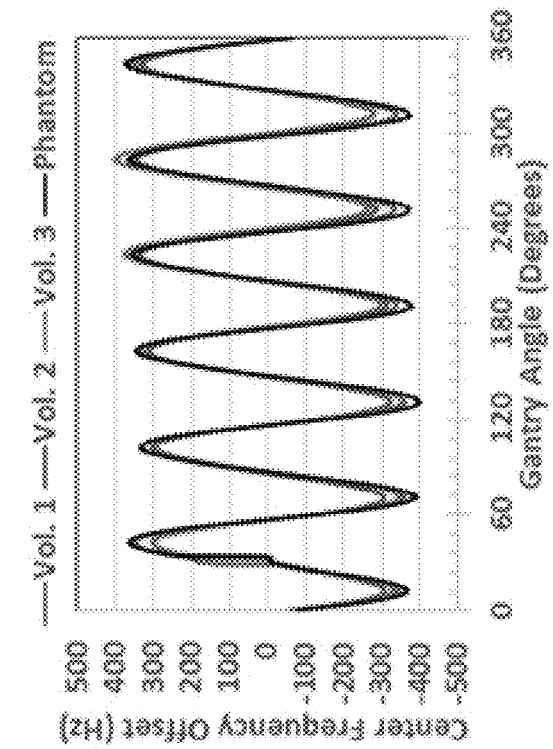
FIG. 8A is a graph summarizing center frequency offsets measured using FID navigators in 3 volunteers and the QUASAR phantom during clockwise gantry rotation, and plotted by gantry angle. The discontinuities at gantry angles 30° and 33° gantry rotations are caused by acceleration/deceleration of the gantry and long time constant B0 eddy currents. The gantry does not travel to angles 31° and 32° by design.
Figure 8B:
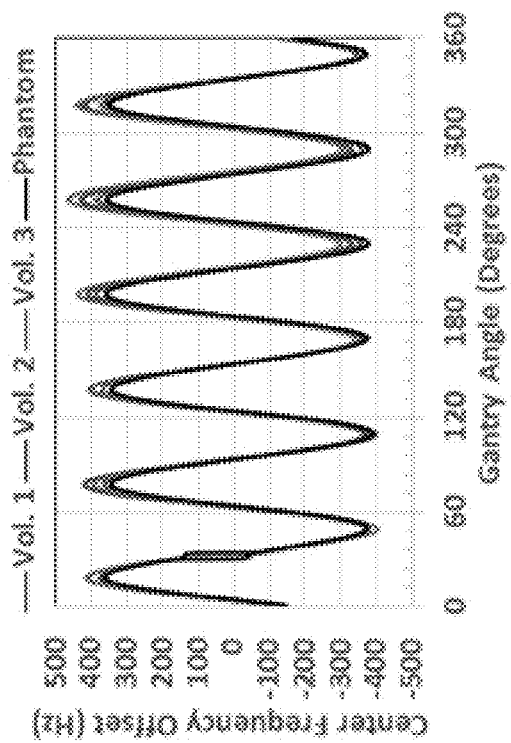
FIG. 8B is a graph summarizing center frequency offsets measured using FID navigators in 3 volunteers and the QUASAR phantom during counterclockwise gantry rotation, and plotted by gantry angle.

FIGS. 8A and 8B summarizes the measured central frequency offsets measured from the phantom for clockwise and counterclockwise gantry rotations, respectively. maximum peak-to-peak (pk-pk) amplitudes of the center frequency offsets were 757 Hz (CW) and 773 Hz (CCW) in the QUASAR phantom. The repeatability of the FID navigator center frequency measured in the QUASAR phantom was <2 Hz based on the root mean squared error (RMSE) of repeated measurements.

Figure 9:
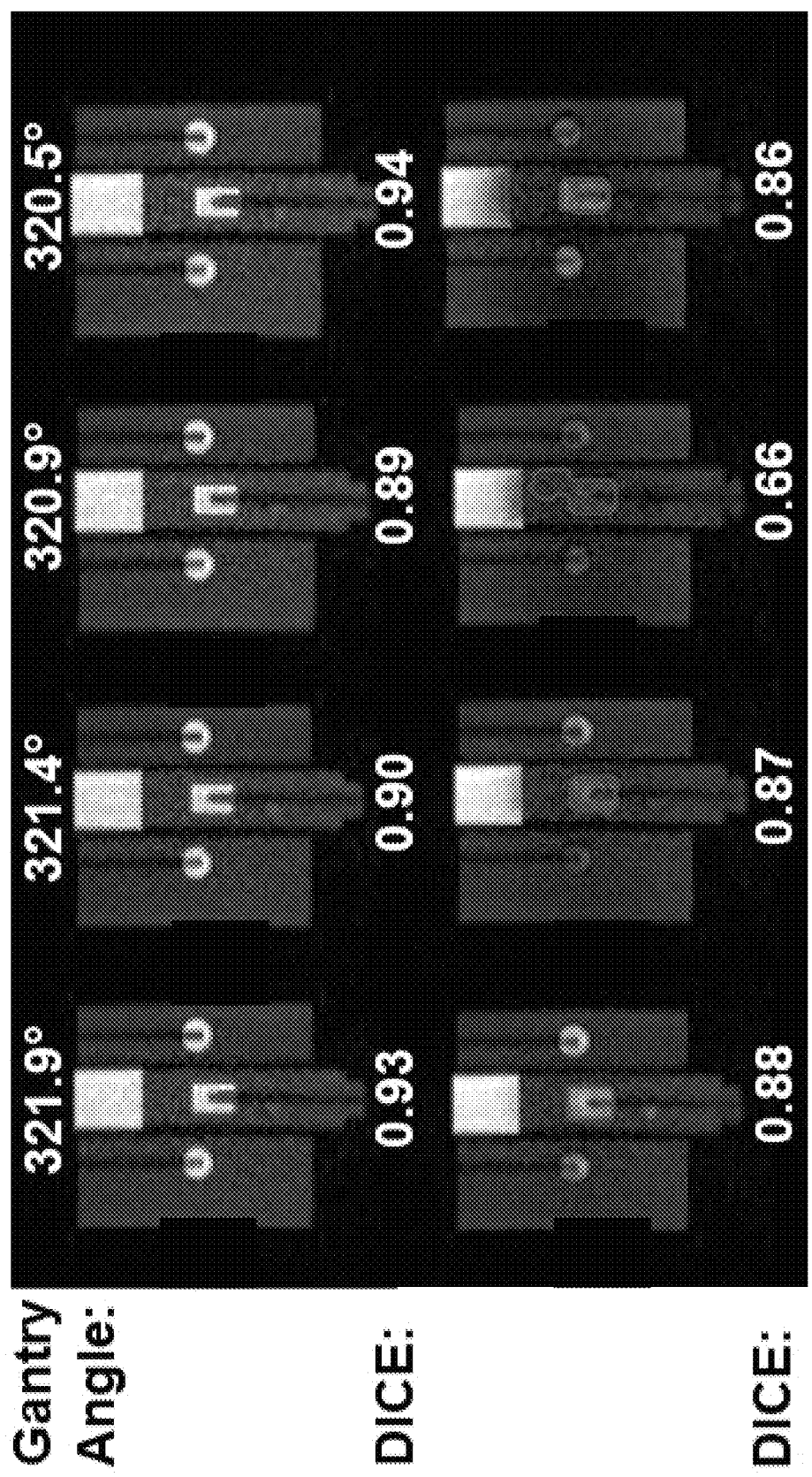
FIG. 9 contains four successive frames (left to right, top row) of a 2D bSSFP sequence (7.3 fps) with real time B0 compensation during counterclockwise gantry rotation (left to right, top row) in the QUASAR phantom. The scan repeated without B0 compensation suffers from artifacts and signal losses during gantry rotation (left to right, bottom row). The Dice coefficients were calculated for the inferior contour (red boundary) at the indicated gantry angles.
Figure 10E:
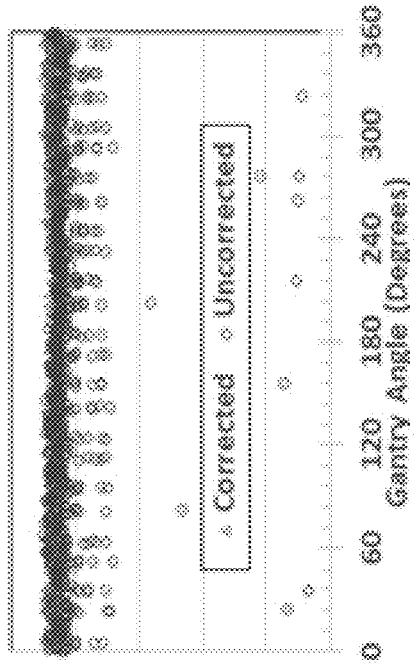
FIG. 10E is a graph of QUASAR phantom results summarizing Dice coefficients for the anterior contours during clockwise rotation while acquiring 2D bSSFP MRIs at 7.3 fps. The B0 correction (Δ) resulted in consistent Dice coefficients compared to images acquired without real-time B0 correction (O).
Figure 10F:
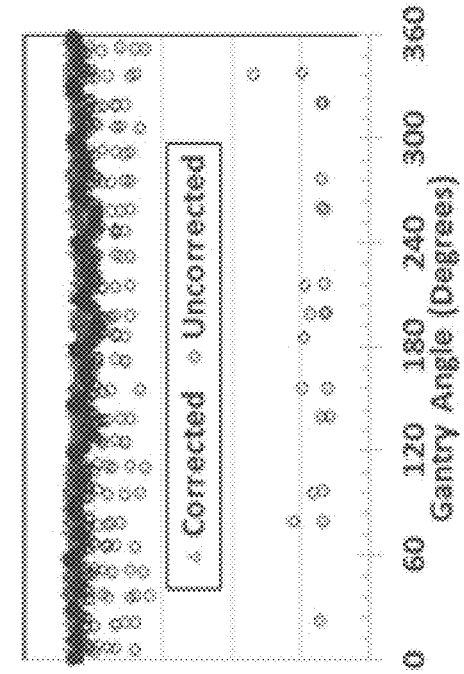
FIG. 10F is a graph of QUASAR phantom results summarizing Dice coefficients for the anterior contours during counterclockwise gantry rotation while acquiring 2D bSSFP MRIs at 7.3 fps. The B0 correction (Δ) resulted in consistent Dice coefficients compared to images acquired without real-time B0 correction (O).
Figure 10G:
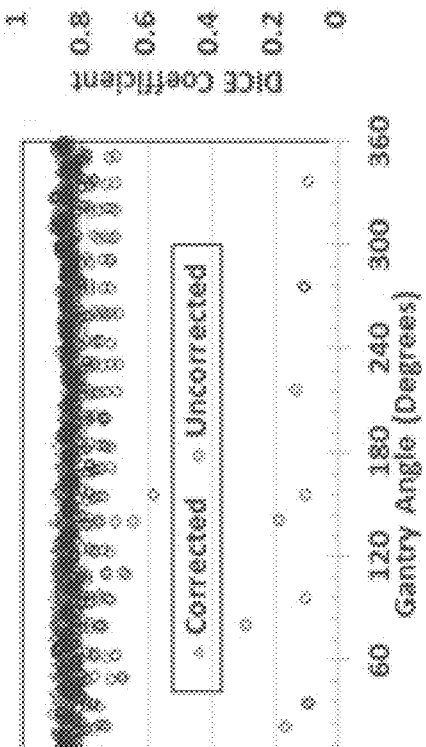
FIG. 10G is a graph of QUASAR phantom results summarizing Dice coefficients for the posterior contours during clockwise gantry rotation while acquiring 2D bSSFP MRIs at 7.3 fps. The B0 correction (Δ) resulted in consistent Dice coefficients compared to images acquired without real-time B0 correction (O).
Figure 10H:
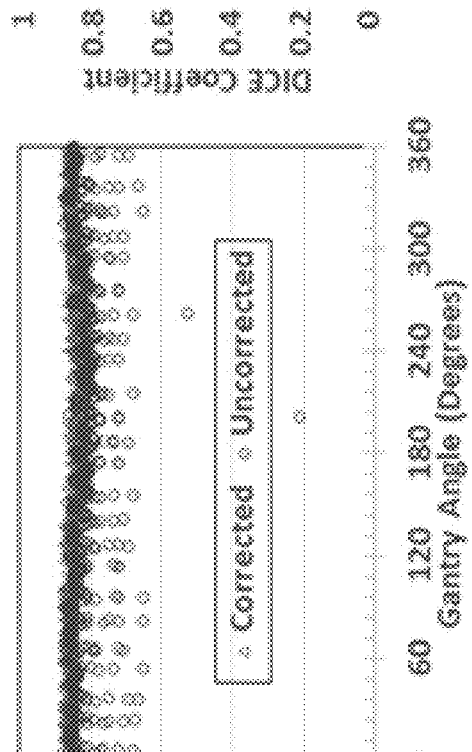
FIG. 10H is a graph of QUASAR phantom results summarizing Dice coefficients for the posterior contours during counterclockwise gantry rotation while acquiring 2D bSSFP MRIs at 7.3 fps. The B0 correction (Δ) resulted in consistent Dice coefficients compared to images acquired without real-time B0 correction (O).

FIG. 9 shows an example of the benefits of B0 compensation in image quality, Dice coefficient, and contour reproducibility for the QUASAR phantom during gantry rotation. In FIGS. 10A, 10B, 10C, 10D, 19E, 10F, 10G, and 10H, the Dice coefficients with versus without B0 compensation are plotted based on gantry angle and gantry rotation direction for the four contours in the QUASAR phantom. All of the contours imaged with B0 compensation met the 0.7 Dice coefficient threshold for imaging performance. Without B0 compensation, Dice coefficients were <0.7 from 0 to 6% of the time, depending on the contour. Mean Dice coefficients, averaged over the entire gantry rotation, are presented in Table II based on the contour, gantry rotation direction, and use of B0 compensation. All paired t-tests (with vs. without B0 compensation) had p<<0.001 thus demonstrating a significant benefit from the B0 compensation in the phantom.

TABLE II

Effects of B0 compensation on mean Dice coefficient for each phantom contour region versus gantry rotation direction.

| | Mean Dice Coefficient (SD) | | | |
|---|---|---|---|---|
| | With $B_0$ Correction | | Without $B_0$ Correction | |
| Contour | CW | CCW | CW | CCW |
| Inferior | 0.92 (0.02) | 0.92 (0.02) | 0.88 (0.09) | 0.89 (0.04) |
| Superior | 1.00 (0.00) | 1.00 (0.00) | 0.98 (0.02) | 0.99 (0.02) |
| Anterior | 0.86 (0.02) | 0.86 (0.02) | 0.83 (0.09) | 0.82 (0.09) |
| Posterior | 0.85 (0.01) | 0.85 (0.01) | 0.80 (0.12) | 0.82 (0.05) |

CW: Clockwise, CCW: Counterclockwise, SD: standard deviation. All paired t-tests had p << 0.001.

Figure 12A:
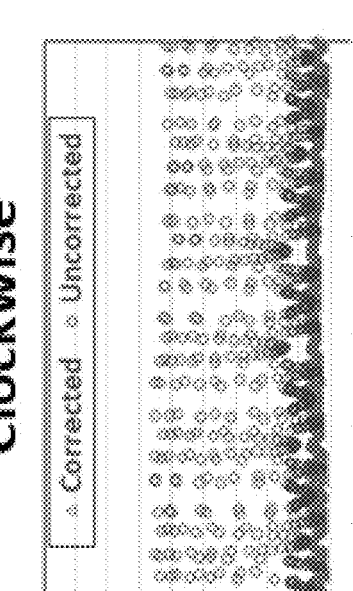
FIG. 12A is a graph of nRMSEs measured with (green Δ) and without (red O) B0 compensation for clockwise gantry rotation using the QUASAR phantom.
Figure 12B:
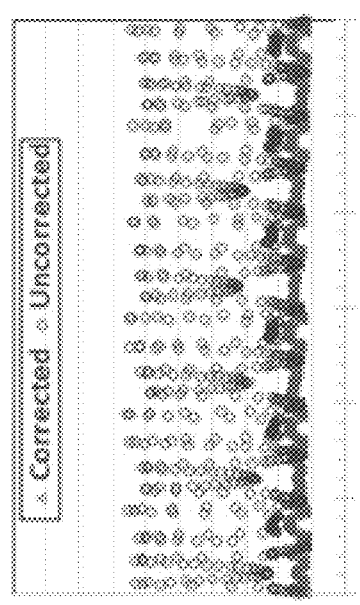
FIG. 12B is a graph of nRMSEs measured with (green Δ) and without (red O) B0 compensation for counterclockwise gantry rotation using the QUASAR phantom.
Figure 12C:
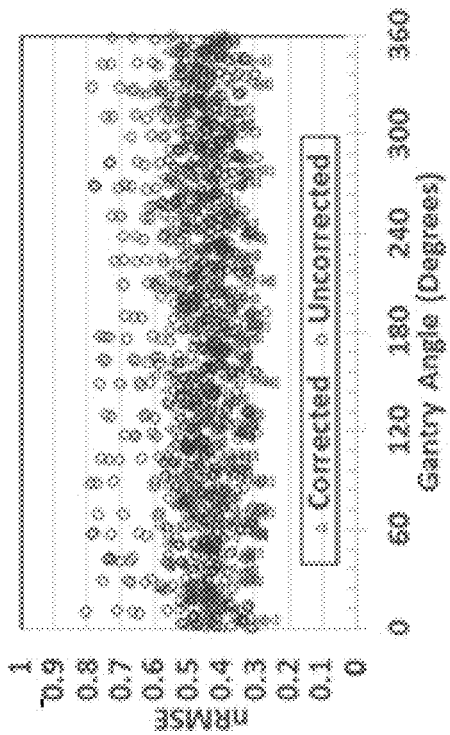
FIG. 12C is a graph of nRMSEs measured with (green Δ) and without (red O) B0 compensation for clockwise gantry rotation obtained in vivo from Volunteer 1.
Figure 12D:
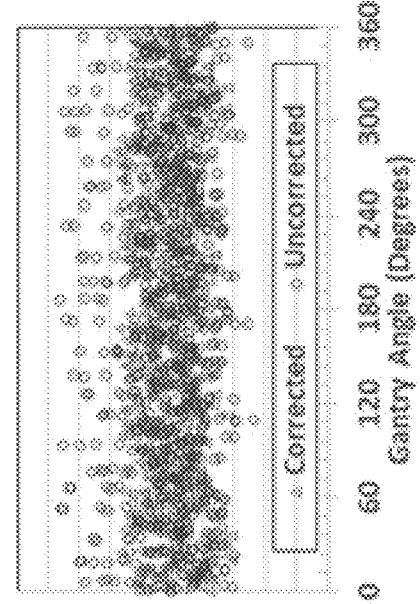
FIG. 12D is a graph of nRMSEs measured with (green Δ) and without (red O) B0 compensation for counterclockwise gantry rotation obtained in vivo from Volunteer 1.
Figure 12E:
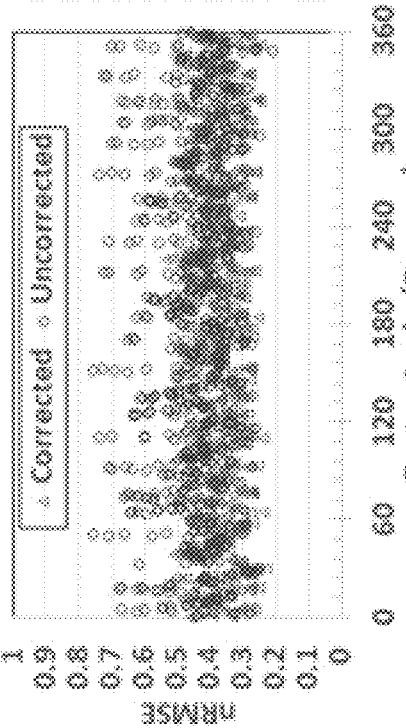
FIG. 12E is a graph of nRMSEs measured with (green Δ) and without (red O) B0 compensation for clockwise gantry rotation obtained in vivo from Volunteer 2.
Figure 12F:
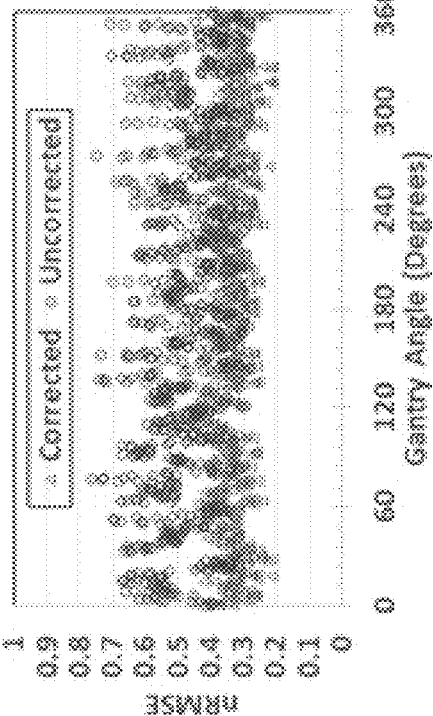
FIG. 12F is a graph of nRMSEs measured with (green Δ) and without (red O) B0 compensation for counterclockwise gantry rotation obtained in vivo from Volunteer 2.
Figure 12G:
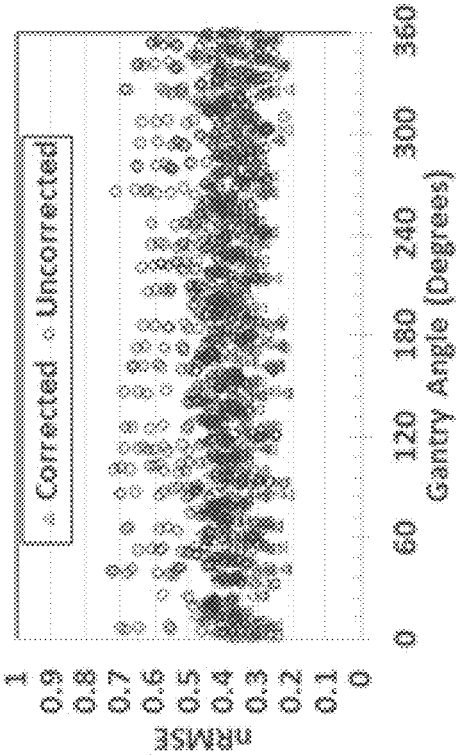
FIG. 12G is a graph of nRMSEs measured with (green Δ) and without (red O) B0 compensation for clockwise gantry rotation obtained in vivo from Volunteer 3.
Figure 12H:
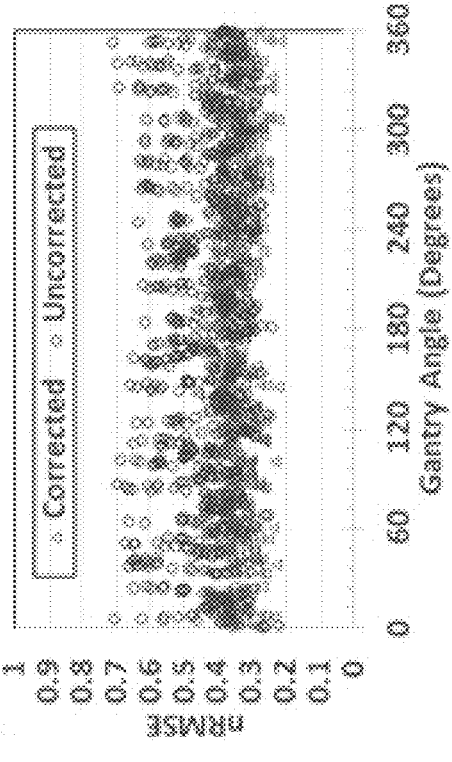
FIG. 12H is a graph of nRMSEs measured with (green Δ) and without (red O) B0 compensation for counterclockwise gantry rotation obtained in vivo from Volunteer 3.

FIGS. 12A and 12B illustrate the reduction in nRMSE with real-time B0 compensation in QUASAR phantom during gantry rotation with versus without B0 compensation are plotted as a function of gantry angle and gantry rotation direction. The changes in mean nRMSEs (i.e., averaged over the entire gantry rotation) resulting from B0 compensation are compared for the QUASAR phantom and the three volunteers in Table III. Real-time B0 compensation resulted in reductions in mean nRMSEs of 51% and 16% for the QUASAR phantom and in vivo, respectively. All paired t-tests had p<<0.001 except for Volunteer 1's counterclockwise gantry rotation measurements (p=0.51).

Table III. Effects of B0 compensation on mean nRMSE for the QUASAR phantom
versus gantry rotation direction.

Example 2: Correction of EMI-Related B0 Field Variations on In Vivo Images

To demonstrate the feasibility of using FID navigators to correct center frequency offsets and minimize the effects of gantry rotation on image quality of in vivo images, the following experiments were conducted.

MRIs were performed as described in Example 1 on three healthy adult volunteers (one female, ages 37-58, weights 66-75 kg) using the 2D bSSFP sequence protocol both with and without B0 compensation. The volunteers were imaged head first supine with the anterior and posterior receiver coils positioned for imaging the thorax and upper abdomen. Scans were performed with the volunteers' arms at their sides to increase volunteer comfort. Acquisitions were acquired with the gantry rotating fully clockwise (CW) and counterclockwise (CCW). Volunteers were also imaged using ViewRay's 4 frames per second (fps) Cartesian and 8 fps radial sequences (see Table I) with the gantry stationary at its home position(300°) to compare their SNRs with the FID navigator Cartesian sequence. The SNR was calculated using the two-image difference method for an ROI placed in the liver.

nRMSEs were calculated for an ROI encompassing the body with and without B0 compensation. Paired t-tests were performed between nRMSE measurements acquired with and without B0 compensation.

As illustrated in FIGS. 8A and 8B, the central frequency offsets measured during the volunteer scans were generally consistent with the phantom measurements. However, the maximum peak-to-peak (pk-pk) amplitudes of the center frequency offsets were 757 Hz (CW) and 773 Hz (CCW) in the QUASAR phantom, and 871 Hz (CW) to 760 Hz (CCW) in vivo. The repeatability of the center frequency offset measurements in vivo was <3 Hz (RMSE) and included variations associated with physiologic motion.

FIGS. 11A, 11B, 11C, and 11D (with real time B0 compensation) and FIGS. 11E, 11F, 11G, and 11H (without compensation) illustrate the reduction in nRMSE with real-time B0 compensation in vivo. The nRMSEs as a function of gantry angle for the in vivo imaging of FIGS. 12C, 12D, 12E, 12F, 12G, and 12H (volunteers 1, 2, and 3) with and without B0 compensation are compared to corresponding nRMSEs obtained for the phantom (FIGS. 12A and 12B). The changes in mean nRMSEs (i.e., averaged over the entire gantry rotation) resulting from B0 compensation are summarized for the QUASAR phantom and the three volunteers in Table III below. Real-time B0 compensation resulted in reductions in mean nRMSEs of 51% and 16% for the QUASAR phantom and in vivo, respectively. All paired t-tests had $p<<0.001$ except for Volunteer 1's counterclockwise gantry rotation measurements ($p=0.51$).

TABLE III

Effects of B0 compensation on mean nRMSE for the QUASAR phantom versus gantry rotation direction.

| ROI | Mean nRMSE (SD) | | | |
| --- | --- | --- | --- | --- |
| | With $B_0$ Correction | | Without $B_0$ Correction | |
| | CW | CCW | CW | CCW |
| Phantom | 0.15 (0.01) | 0.15 (0.02) | 0.29 (0.14) | 0.32 (0.15) |
| Volunteer 1 | 0.42 (0.08) | 0.51 (0.08) | 0.48 (0.11) | 0.51 (0.12) |
| Volunteer 2 | 0.37 (0.06) | 0.36 (0.06) | 0.43 (0.10) | 0.44 (0.10) |
| Volunteer 3 | 0.35 (0.05) | 0.34 (0.05) | 0.44 (0.10) | 0.49 (0.10) |

For the three volunteers, the SNR (8.8±1.45) of the 7.3 fps FID navigator Cartesian sequence was about half of the 4 fps Cartesian (20.05±2.52) and 8 fps radial (20.17±2.57) sequences.

Example 3: Evaluation and Correction of EMI-Related B0 Field Variations Using Spherical Phantom To measure and correct the EMI-related $B_0$ field variations in real time associated with the gantry position in a balanced steady state free precession (bSSFP) sequence, the following experiments were conducted.

A hard pulse navigator (FA:70, dwell time=8 µs, complex points=64) was added to a 2D Cartesian bSSFP sequence preceding each image acquisition on a ViewRay 0.35 T MRI-Linac. Measurements were performed using a spherical 24 cm DSV phantom doped with 5 mM NiSO4(T1/T2: 330/260 ms) using phased array torso coils designed for use in the MR-IGRT system. Phase data from the first navigator was used as a reference, and the central frequency offset was determined using phase data from each subsequent navigator. The frequency offset was then passed back to the sequence from the image calculation computer as a real time feedback object and used to adjust the resonant frequency for the bSSFP image pulses and receiver. B0 fluctuations as a result of EMI were measured by allowing the gantry to rotate uninterrupted counterclockwise from 30° to 33°. In addition, the B0 variations due to a stationary gantry were evaluated from 30° to 33° in 15° increments. Shimming for both experiments was performed at gantry angle 30° prior to gantry rotation. The calculated central frequency offsets from the bSSFP navigators were compared against shifts in the peak frequency from a pair of FID sequences (rBW=4 Hz/point for EMI induced B0 offsets and rBW=1 Hz/point for stationary gantry related B0 offsets). Linear interpolation was used to align the time bases of the navigator and of the FID data for comparison.

Figure 25:
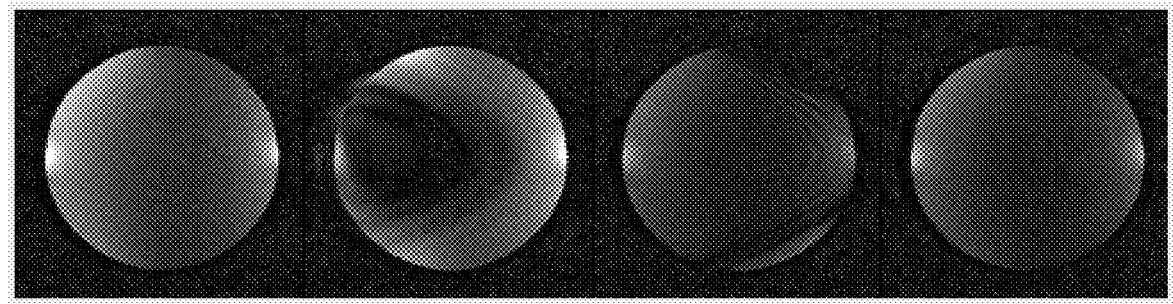
FIG. 25 contains four successive MRI frames (from left to right) depicting the null band artifacts caused by EMI while rotating a radiation therapy gantry in a 2D sagittal bSSFP sequence (TE/TR: 1.7/3.4, FA: 70°, rBW: 558 Hz/pixel).
Figure 26:
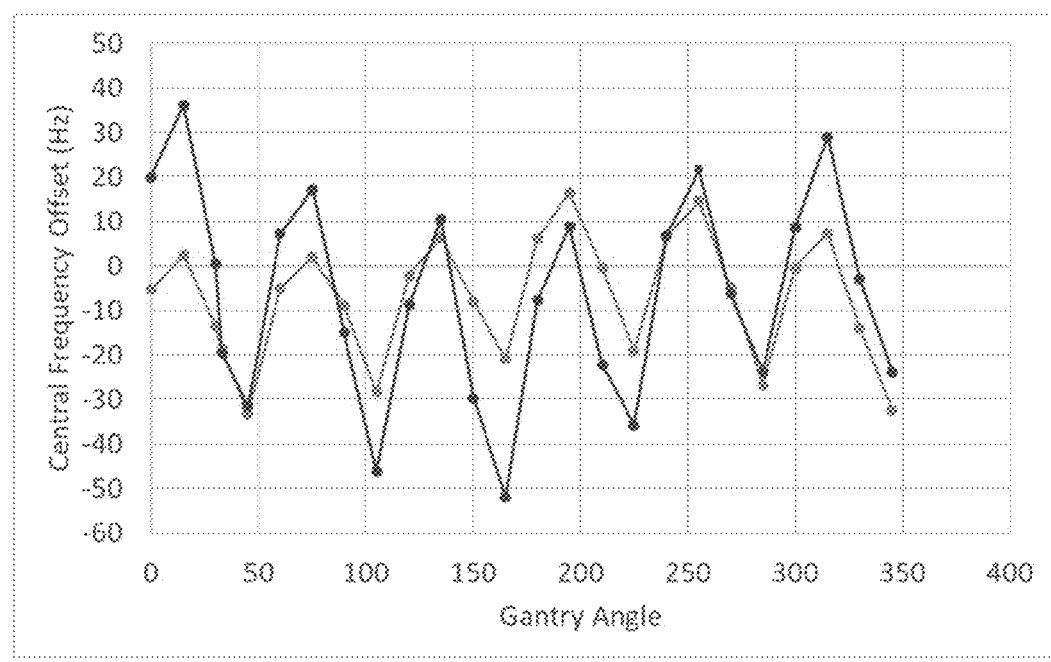
FIG. 26 is a graph summarizing resonant frequency offset due to gantry angle calculated using the navigator added to the bSSFP sequence (red) and using a FID sequence (blue).
Figure 27:
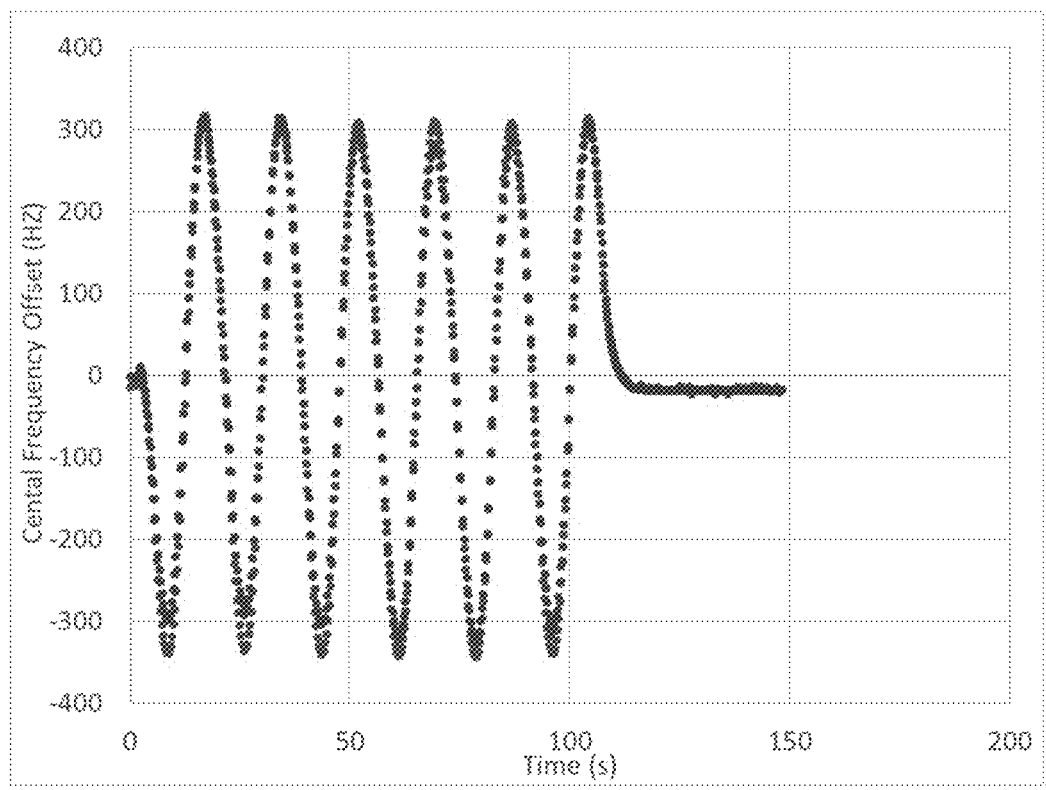
FIG. 27 is a graph summarizing resonant frequency offset during gantry rotation starting at 30° and rotating around counterclockwise back to 33°. Offsets were calculated using a navigator inserted into a bSSFP sequence (red) and by measuring the peak offset in a FID sequence (blue).

FIG. 25 shows a series of images of the phantom obtained during gantry rotation. Central frequency shifts calculated using the inserted bSSFP navigators showed similar results as the reference FID data both while the gantry was rotating (RMSE=20.9 Hz, FIG. 26) and while the gantry was stationary (RMSE=15.5 Hz, FIG. 27). The EMI from gantry rotation resulted in B0 offsets about 10 times larger than the B0shifts due to the stationary gantry position. Both sets of B0 offsets displayed sinusoidal behavior with a period of 60°. This behavior corresponds to the six 227 kg mu-metal shield buckets on the MRI-Lina that are spaced 60° apart and house accelerator components.

Example 3: Evaluation of EMI-Related B0 Field Variations Using EM Model

To evaluate EMI-related $B_0$ field variations in real time associated with the gantry position in a balanced steady state free precession (bSSFP) sequence, the following experiments were conducted.

An EM model of the MRI-Linac was created using CAD data from ViewRay. EM modeling was performed using FEniCS, an open source finite element modeling (FEM) package. Specifically, three-dimensional numerical simulations of the time-dependent Maxwell-equations to model the main magnetic field (B0) and the effects of the gradient fields and coils, passive shims, mu-metal and RF shields, cryostat, gantry motor, and rotating gantry will be performed. Field camera measurements were used to calibrate the EM model for static and rotating gantry cases.

Figures 18A, 18B, 18C:
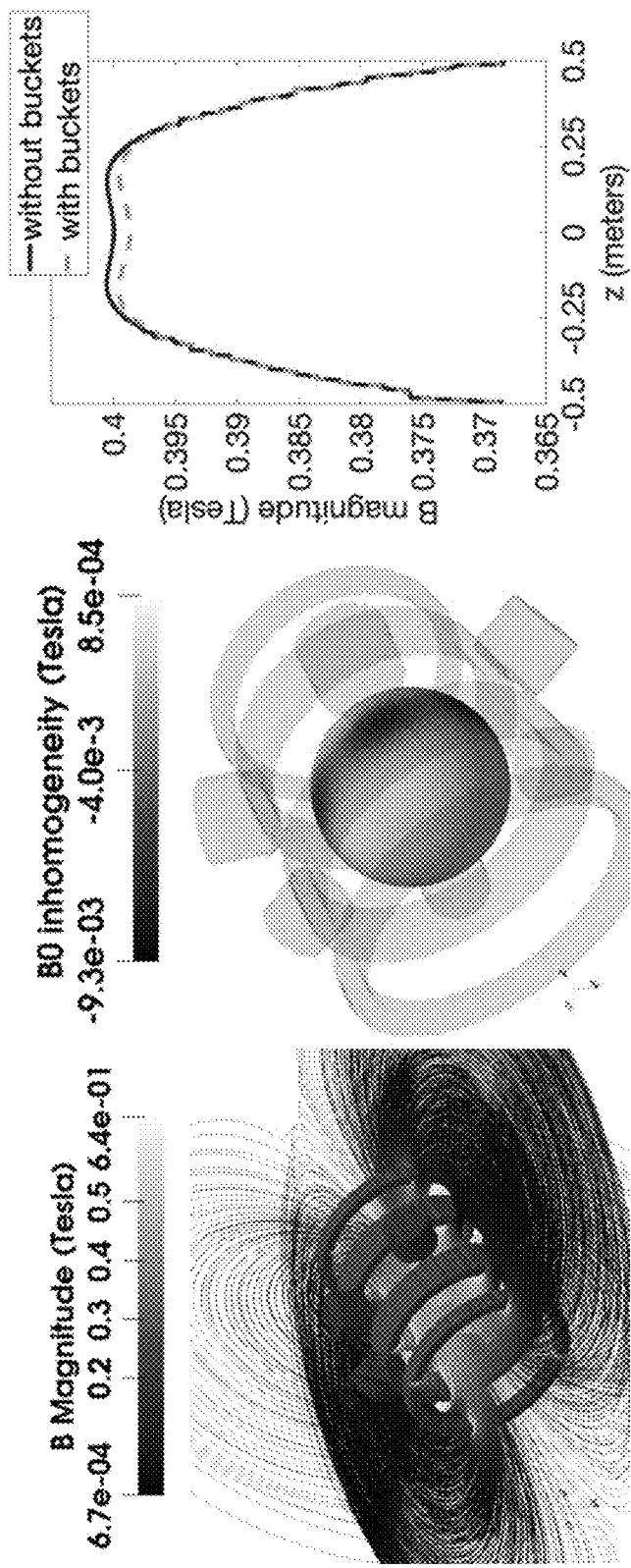
FIG. 18A is a map of fringe field streamlines obtained using an EM simulation of a stylized MRI-Linac system.
FIG. 18B is a map of B0 inhomogeneity on the surface of a 0.5 m DSV obtained using an EM simulation of a stylized MRI-Linac system.
FIG. 18C is a 1D profile of B0 as a function of distance from center obtained using an EM simulation of a stylized MRI-Linac system.
Figures 19A, 19B, 19C:
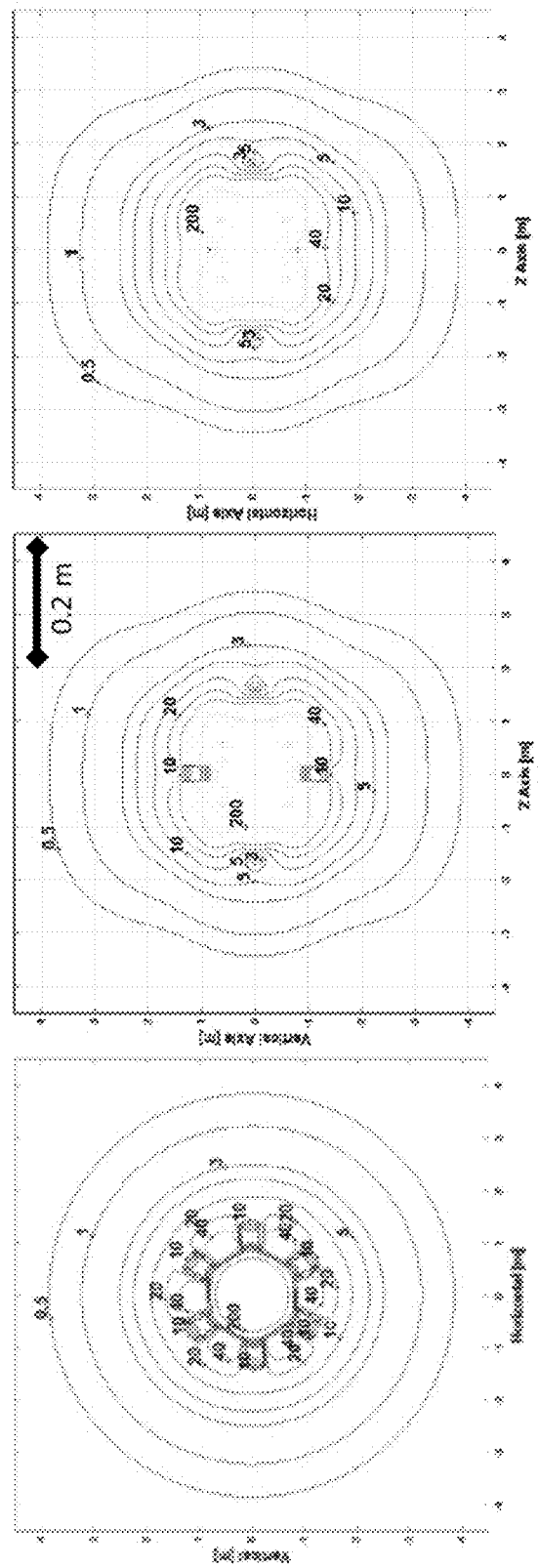
FIG. 19A is an axial fringe field map (in mT) of an MRI-Linac system.
FIG. 19B is a coronal fringe field map (in mT) of an MRI-Linac system.
FIG. 19C is a sagittal fringe field map (in mT) of an MRI-Linac system.
Figure 20:
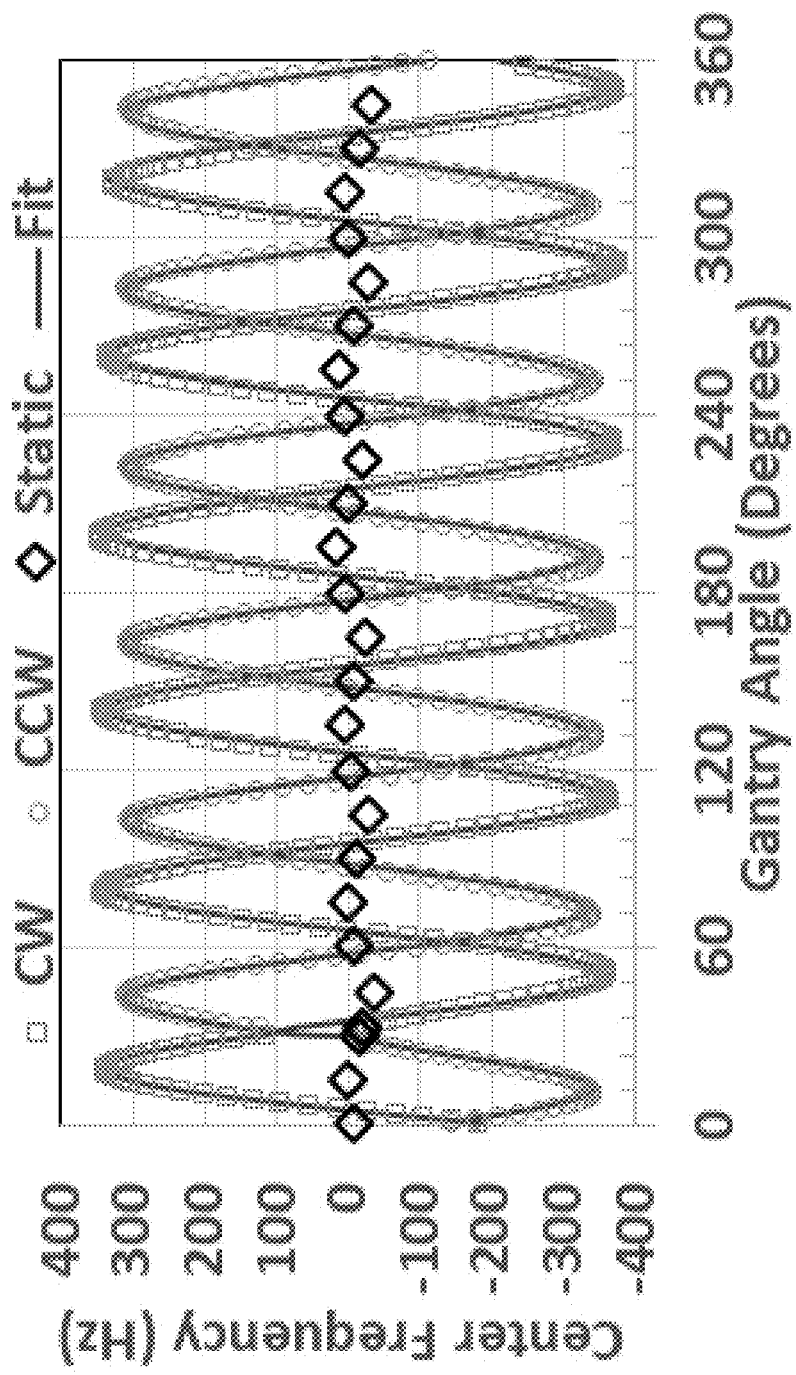
FIG. 20 is a graph of center frequency fluctuations during continuous clockwise (CW) and counter CW (CCW) gantry rotation in 24 cm DSV phantom by acquiring free induction decays every 0.29 s highlight the system's 12-pole behavior. The results are fit to the sinusoid function and compared to that of a static gantry.
Figure 21:
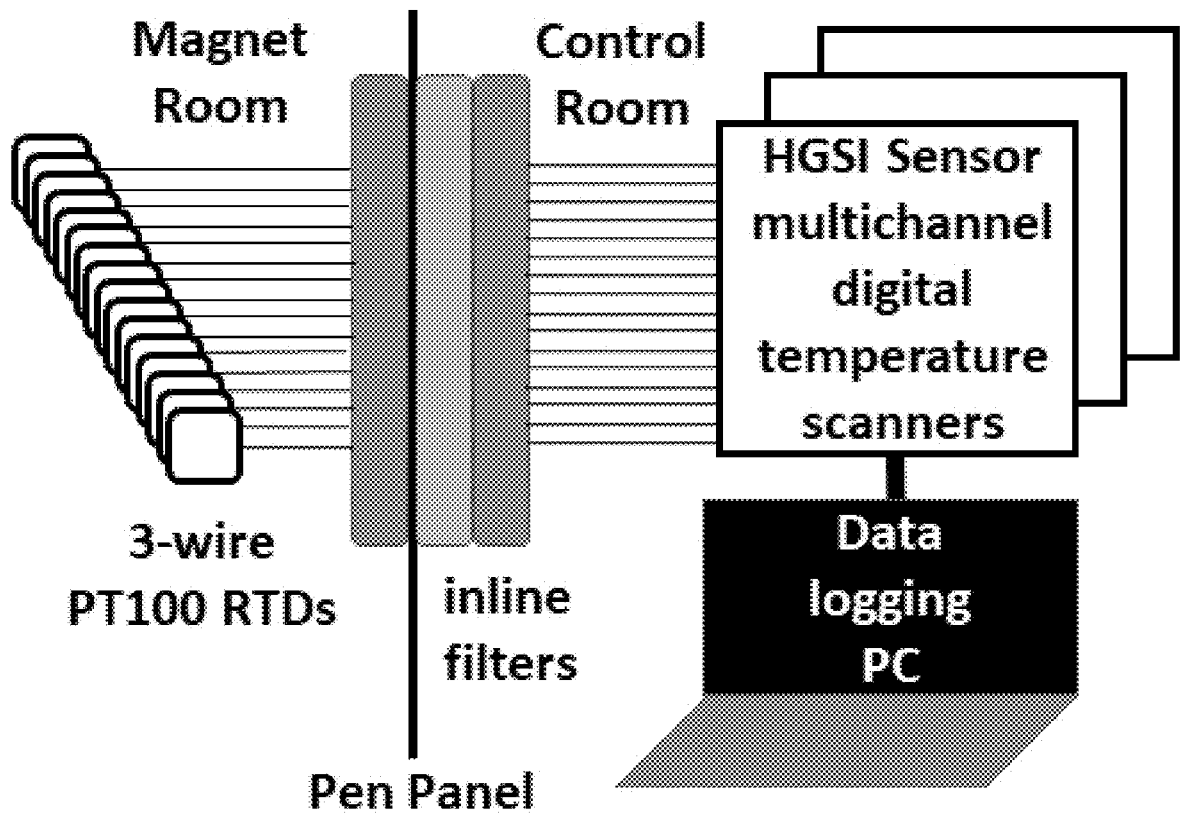
FIG. 21 is a schematic illustration showing the thermometry equipment used to obtain simultaneous measurements from 80 RTD sensors

FIGS. 18A, 18B, and 18C present preliminary EMI modeling on a stylized geometry consisting of the four main magnet superconducting coil windings and six mu-metal shields. The stylized MRI-Linac system was placed at the center of the computational domain, a sphere of four-meter radius. The computational domain was then discretized using ~20M tetrahedral elements with the adaptive resolution ranging from 100 mm (fringe field) to 4 mm (near the isocenter). A preliminary calibration of the EM model using fringe field maps provided by ViewRay (FIGS. 19A, 19B, and 19C). Calibration parameters included spatial heterogeneity in magnetic permeability of the different components as well as electric currents in the active shims. The EM model was further refined with direct magnetic field measurements using a kilogauss meter (AlphaLab Inc. Model GM2).

The B0 fluctuations associated with the gantry rotation were modeled based on the gantry velocity ($\omega$), acceleration ($\alpha$), angle ($\theta$), rotation direction (r):

$$B_0(\theta, \omega, \alpha, r) = A(\omega) \cdot \sin\left(\frac{B(\alpha)t^2}{2} + C(\omega)t + \varphi(r)\right) + D(r)$$

where A, B, C, D, and $\varphi$ are fitting parameters related to the gantry kinematics, the gantry accelerated at 2.6°/s2 to a speed of 3.4°/s. Deceleration was variable.

What is claimed is:

1. A method for obtaining high-quality MR images for guidance of a treatment using an MR-IGRT system, the method comprising for each frame of a cine data MR data acquisition sequence:
   producing, using the MR-IGRT system, a non-selective RF excitation pulse;
   detecting, using the MR-IGRT system, a plurality of free induction decay (FID) signals;
   calculating a center frequency offset based on the plurality of free induction decay (FID) signals;
   modifying the image acquisition selective excitation RF pulses and receiver phase based on the center frequency offset;
   obtaining an MR image dataset using the modified image acquisition selective excitation RF pulses and receiver phase; and
   reconstructing a frame of the MR image, wherein the MR image comprises reduced EMI artifacts associated with gantry motion.

2. The method of claim 1, wherein the non-selective RF excitation pulse is selected from a rectangular excitation pulse, an apodized sinc pulse, or an adiabatic pulse.

3. The method of claim 2, wherein the non-selective RF excitation pulse is the rectangular excitation pulse with a duration of less than about 0.5 ms and a flip angle of no more than about 30°.

4. The method of claim 3, further comprising producing at least one magnetization restoration pulse prior to obtaining the MR image dataset using the modified image acquisition selective excitation RF pulses and receiver phase.

5. The method of claim 4, wherein the center frequency offset $\Delta f$ is calculated using the equation:

$$\Delta f = \frac{1}{2\pi(N-k+1)} \sum_{i=k}^{N} \frac{d(\phi_{new,i} - \phi_{ref,i})}{dt}$$

where $\phi_{new}$ is a most recent unaliased FID navigator phase, and $\phi_{ref}$ is an unaliased reference FID navigator phase.

6. The method of claim 5, wherein the transmitter/receiver phase of each imaging sequence is adjusted for each excitation using the equation:

$$\phi_n = (n-1) \cdot \Delta f \cdot TR \cdot 360° + \phi_{cycle}$$

where $\Phi_n$ is a phase increment in degrees for the nth excitation, TR is a repetition time, $\Delta f$ is a central frequency offset obtained from a previous measurement, and $\phi_{cycle}$ is a 0°/180° alternating phase.

* * * * *